United States Patent
Baerson et al.

(10) Patent No.: US 6,803,501 B2
(45) Date of Patent: Oct. 12, 2004

(54) **METHODS FOR MAKING PLANTS TOLERANT TO GLYPHOSATE AND COMPOSITIONS THEREOF USING A DNA ENCODING AN EPSPS ENZYME FROM *ELEUSINE INDICA***

(75) Inventors: Scott R. Baerson, Oxford, MS (US); Damian J. Rodriguez, Lebanon, IL (US); Gregory R. Heck, Crystal Lake Park, MO (US)

(73) Assignee: Monsanto Technology, LLC, St. Louis, MO (US)

( * ) Notice: Subject to any disclaimer, the term of this patent is extended or adjusted under 35 U.S.C. 154(b) by 17 days.

(21) Appl. No.: 09/800,130

(22) Filed: Mar. 6, 2001

(65) Prior Publication Data

US 2003/0188346 A1 Oct. 2, 2003

Related U.S. Application Data

(60) Provisional application No. 60/188,093, filed on Mar. 9, 2000.

(51) Int. Cl.$^7$ .......................... A01H 5/00; C12N 15/29; C12N 15/82
(52) U.S. Cl. ...................... 800/300; 435/418; 536/23.2; 536/23.4; 536/23.6; 800/278; 800/298; 800/300.1
(58) Field of Search ............................... 536/23.4, 23.6, 536/23.2; 435/320.1, 468, 419, 418; 800/278, 287, 298, 300, 300.1, 320, 320.1–320.3, 323, 312, 314–316, 317.2, 317.3, 317.4

(56) References Cited

U.S. PATENT DOCUMENTS 5,627,061 A * 5/1997 Barry et al. ................. 800/288

FOREIGN PATENT DOCUMENTS

| WO | WO 97/04103 | 2/1997 |
| WO | WO 98/44140 | 8/1998 |
| WO | WO 98/54330 | 12/1998 |

OTHER PUBLICATIONS

Reeck et al, 1987, Cell 50:667.*
Reeck, G.R., et al, "Homology in Proteins and Nucleic Acids: A Terminology Muddle and a Way out of It," *Cell* 50, 667 (1987).
Lee, L. J., and Ngim, J. "A First Report of Glyphosate–Resistant Goosegrass (*Eleusine indica* (L) Gaertn) in Malaysia," *Pest Management Science* 56:336–339 (2000).
Tran, M.; Baerson, S.; Brinker, R.; Casagrande, L.; Faletti, M.; Feng, Y.; Nemeth, M.; Reynolds, T.; Rodriguez, D.; Schafer, D.; Stalker, D.; Taylor, N.; Teng, Y.; and G. Dill, "Characterization of Glyphosate Resistant *Eleusine indica* Biotypes from Malaysia", Proceedings of the Seventeenth Asian–Pacific Weed Science Society Conference, pp. 527–536 (1999).
Teng, Y.–T.; and K.C. Teo, "Weed Control and Management of Resistant Goosegrass (*Eleusine indica*) in Malaysia"; in Proceedings of the Seventeenth Asian–Pacific Weed Science Society Conference, pp. 753–758 (1999).

* cited by examiner

*Primary Examiner*—Amy J. Nelson
*Assistant Examiner*—David H Kruse
(74) *Attorney, Agent, or Firm*—Grace Bonner; Howrey Simon Arnold & White, LLP

(57) ABSTRACT

The methods and materials disclosed herein are directed to glyphosate herbicide tolerance in plants. In particular, the isolation of a glyphosate resistant EPSP synthase coding sequence from *Eleusine indica*. The coding sequence is useful to genetically engineer plants for tolerance to glyphosate herbicide.

12 Claims, 14 Drawing Sheets

```
  1  GCGGGGCGCGG AGGAGGTGGT GCTGCAGCCC ATCAAGGAGA TCTCCGGCGT
 51  CGTGAAGCTG CCGGGGTCCA AGTCGCTCTC CAACCGGATC CTCCTGCTCT
101  CCGCCCTCGC CGAGGGAACA ACTGTGGTGG ATAACCTTTT AAACAGTGAG
151  GACGTCCACT ACATGCTCGG GGCCCTGAAA ACCCTCGGAC TCTCTGTGGA
201  AGCGGACAAA GCTGCCAAAA GAGCGGTAGT TGTTGGCTGT GGTGGCAAGT
251  TCCCAGTTGA GAAGGATGCG AAAGAGGGAGG TGCAGCTCTT CTTGGGGAAT
301  GCTGGAACTG CAATGCGATC ATTGACAGCA GCCGTAACTG CTGCTGGAGG
351  AAATGCAACT TATGTGCTTG ATGGAGTGCC AAGAATGCGG GAGAGACCCA
401  TTGGCGACTT GGTTGTCGGA TTGAAACAGC TTGGTGCGGA TGTTGATTGT
451  TTCCTTGGCA CTGACTGCCC ACCTGTTCGT GTCAAGGGAA TCGGAGGGCT
```

FIG. 1-A

```
 501  ACCTGGTGGC AAGGTTAAGT TATCTGGTTC CATCAGCAGT CAGTACTTGA
 551  GTGCCTTGCT GATGGCTGCT CCTTTAGCTC TTGGGGATGT GGAGATTGAA
 601  ATCATTGATA AACTGATCTC CATCCCTTAT GTTGAAATGA CATTGAGATT
 651  GATGGAGCGT TTTGGCGTGA AAGCAGAGCA TTCTGATAGC TGGGACAGAT
 701  TCTACATCAA GGGAGGTCAA AAATACAAGT CCCCTAAAAA TGCCTACGTG
 751  GAAGGTGATG CCTCAAGTGC GAGCTATTTC TTGGCTGGTG CTGCAATCAC
 801  TGGAGGGACT GTGACTGTTG AAGGTTGTGG CACCACCAGT CTGCAGGGTG
 851  ATGTGAAATT TGCCGAGGTA CTCGAGATGA TGGGAGCGAA GGTTACATGG
 901  ACTGAAACTA GCGTAACTGT TACCGGTCCA CAACGTGAGC CATTTGGGAG
 951  GAAACACCTA AAAGCTATTG ATGTTAACAT GAACAAAATG CCCGATGTCG
1001  CCATGACTCT TGCCGTGGTT GCCCTATTTG CTGATGGCCC AACTGCTATC
```

FIG. 1-B

```
1051  AGAGATGTGG CTTCCTGGAG AGTAAAGGAG ACCGAGAGGA TGGTTGCAAT
1101  CCGGACTGAG CTAACAAAGC TGGGAGCCGTC GGTCGAGGAA GGACTGGACT
1151  ACTGCATTAT CACACCGCCC GAGAAGCTGA ACGTAACGGC CATCGACACC
1201  TACGATGACC ACAGGATGGC CATGGCCTTC TCCCTCGCCG CCTGCGCCGA
1251  CGTGCCTGTG ACCATCCCGG ACCCCGGCTG CACCCGCAAG ACCTTCCCAG
1301  ACTACTTCGA CGTGCTGAGC ACTTTCGTCA AGAACTAA
```

FIG. 1-C

```
  1  AGAEEVVLQP IKEISGVVKL PGSKSLSNRI LLLSALAEGT TVVDNLLNSE
 51  DVHYMLGALK TLGLSVEADK AAKRAVVVGC GGKFPVEKDA KEEVQLFLGN
101  AGTAMRSLTA AVTAAGGNAT YVLDGVPRMR ERPIGDLVVG LKQLGADVDC
151  FLGTDCPPVR VKGIGGLPGG KVKLSGSISS QYLSALLMAA PLALGDVEIE
201  IIDKLISIPY VEMTLRLMER FGVKAEHSDS WDRFYIKGGQ KYKSPKNAYV
251  EGDASSASYF LAGAAITGGT VTVEGCGTTS LQGDVKFAEV LEMMGAKVTW
301  TETSVTVTGP QREPFGRKHL KAIDVNMNKM PDVAMTLAVV ALFADGPTAI
351  RDVASWRVKE TERMVAIRTE LTKLGASVEE GLDYCIITPP EKLNVTAIDT
401  YDDHRMAMAF SLAACADVPV TIRDPGCTRK TFPDYFDVLS TFVKN*
```

```
  1 AGAEEVVLQPIKEISGVVKLPGSKSLSNRILLLSALAEGTTVVDNLLNSE  50
    ||||||||||||||||||||||||||||||||||||||||||||||||||
  1 AGAEEVVLQPIKEISGVVKLPGSKSLSNRILLLSALAEGTTVVDNLLNSE  50

51 DVHYMLGALKTLGLSVEADKAAKRAVVVGCGGKFPVEKDAKEEVQLFLGN 100
    ||||||||||||||||||||||||||||||||||||||||||||||||||
 51 DVHYMLGALKTLGLSVEADKAAKRAVVVGCGGKFPVEKDAKEEVQLFLGN 100

101 AGTAMRSLTAAVTAAGGNATYVLDGVPRMRERPIGDLVVGLKQLGADVDC 150
    ||||| ||||||||||||||||||||||||||||||||||||||||||||
101 AGTAMRPLTAAVTAAGGNATYVLDGVPRMRERPIGDLVVGLKQLGADVDC 150

151 FLGTDCPPVRVKGIGGLPGGKVKLSGSISSQYLSALLMAAPLALGDVEIE 200
    ||||||||||||||||||||||||||||||||||||||||||||||||||
151 FLGTDCPPVRVKGIGGLPGGKVKLSGSISSQYLSALLMAAPLALGDVEIE 200

201 IIDKLISIPYVEMTLRLMERFGVKAEHSDSWDRFYIKGGQKYKSPKNAYV 250
    ||||||||||||||||||||||||||||||||||||||||||||||||||
201 IIDKLISIPYVEMTLRLMERFGVKAEHSDSWDRFYIKGGQKYKSPKNAYV 250
```

FIG. 9-A

```
251 EGDASSASYFLAGAAITGGTVTVEGCGTTSLQGDVKFAEVLEMMGAKVTW 300
    ||||||||||||||||||||||||||||||||||||||||||||||||||
251 EGDASSASYFLAGAAITGGTVTVEGCGTTSLQGDVKFAEVLEMMGAKVTW 300

301 TETSVTVTGPQREPFGRKHLKAIDVNMNKMPDVAMTLAVVALFADGPTAI 350
    ||||||||||||||||||||||||||||||||||||||||||||||||||
301 TETSVTVTGPQREPFGRKHLKAIDVNMNKMPDVAMTLAVVALFADGPTAI 350

351 RDVASWRVKETERMVAIRTELTKLGASVEEGLDYCIITPPEKLNVTAIDT 400
    |||||||||||||||||||||||||||||  ||||||||||||||||||
351 RDVASWRVKETERMVAIRTELTKLGASVEEGPDYCIITPPEKLNVTAIDT 400
```

FIG. 9-B

SEQUENCE LISTING

```
<160> NUMBER OF SEQ ID NOS: 16
<210> SEQ ID NO 1
<211> LENGTH: 22
<212> TYPE: DNA
<213> ORGANISM: Artificial sequence
<220> FEATURE:
<221> NAME/KEY: misc_feature
<223> OTHER INFORMATION: n=a or g or c or t
      w=a or t
      s=g or c
      r=g or a, y=t or c
<221> NAME/KEY: exon
<222> LOCATION: (1)..(22)
<223> OTHER INFORMATION: fully synthetic DNA primer

<400> SEQUENCE: 1 tnw sng tng arg cng aya arg t                                    22
Xaa Xaa Xaa Xaa Xaa Xaa Xaa
1               5

<210> SEQ ID NO 2
<211> LENGTH: 23
<212> TYPE: DNA
<213> ORGANISM: Artificial sequence
<220> FEATURE:
<221> NAME/KEY: misc_feature
<223> OTHER INFORMATION: n=a or g or c or t
      k=g or t
      r=g or a
<221> NAME/KEY: exon
<222> LOCATION: (1)..(23)
<223> OTHER INFORMATION: fully synthetic DNA primer

<400> SEQUENCE: 2 gcc atn gcc atn ckr tgr tcr tc                                   23
Ala Xaa Ala Xaa Xaa Xaa Xaa
1               5

<210> SEQ ID NO 3
<211> LENGTH: 24
<212> TYPE: DNA
<213> ORGANISM: Artificial sequence
<220> FEATURE:
<221> NAME/KEY: exon
<222> LOCATION: (1)..(24)
<223> OTHER INFORMATION: fully synthetic DNA primer

<400> SEQUENCE: 3 gtg aaa gca gag cat tct gat agc                                  24
Val Lys Ala Glu His Ser Asp Ser
1               5

<210> SEQ ID NO 4
<211> LENGTH: 29
<212> TYPE: DNA
<213> ORGANISM: Artificial sequence
```

```
<220> FEATURE:
<221> NAME/KEY: exon
<222> LOCATION: (1)..(29)
<223> OTHER INFORMATION: fully synthetic DNA primer

<400> SEQUENCE: 4 ggc tgc tgt caa tgt cgc att gca gtt cc                               29
Gly Cys Cys Gln Cys Arg Ile Ala Val
1               5                   10

<210> SEQ ID NO 5
<211> LENGTH: 32
<212> TYPE: DNA
<213> ORGANISM: Artificial sequence
<220> FEATURE:
<221> NAME/KEY: exon
<222> LOCATION: (1)..(32)
<223> OTHER INFORMATION: fully synthetic DNA primer

<400> SEQUENCE: 5 ctc ttt cgc atc ctt ctc aac tgg gaa ctt gc                           32
Leu Phe Arg Ile Leu Leu Asn Trp Glu Leu
1               5                   10

<210> SEQ ID NO 6
<211> LENGTH: 1338
<212> TYPE: DNA
<213> ORGANISM: Eleusine indica

<400> SEQUENCE: 6
gcgggcgcgg aggaggtggt gctgcagccc atcaaggaga tctccggcgt cgtgaagctg      60
ccggggtcca agtcgctctc aaccggatc ctcctgctct ccgccctcgc cgagggaaca     120 actgtgtgg ataacctttt aaacagtgag gacgtccact acatgctcgg ggccctgaaa     180
accctcggac tctctgtgga agcggacaaa gctgccaaaa gagcggtagt tgttggctgt     240
ggtggcaagt tcccagttga gaaggatgcg aagaggagg tgcagctctt cttggggaat     300
gctggaactg caatgcgatc attgacagca gccgtaactg ctgctggagg aaatgcaact     360
tatgtgcttg atggagtgcc aagaatgcgg gagagaccca ttggcgactt ggttgtcgga     420
ttgaaacagc ttggtgcgga tgttgattgt ttccttggca ctgactgccc acctgttcgt     480
gtcaagggaa tcgagggct acctggtggc aaggttaagt tatctggttc catcagcagt     540
cagtacttga gtgccttgct gatggctgct cctttagctc ttgggatgt ggagattgaa     600 atcattgata aactgatctc catcccttat gttgaaatga cattgagatt gatggagcgt     660
tttggcgtga agcagagca ttctgatagc tgggacagat tctacatcaa gggaggtcaa     720
aaatacaagt cccctaaaaa tgcctacgtg aaggtgatg cctcaagtgc gagctatttc     780
ttggctggtg ctgcaatcac tggagggact gtgactgttg aaggttgtgg caccaccagt     840
ctgcagggtg atgtgaaatt tgccgaggta ctcgagatga tgggagcgaa ggttacatgg     900
actgaaacta gcgtaactgt taccggtcca caacgtgagc catttgggag gaaacaccta     960
aaagctattg atgttaacat gaacaaaatg cccgatgtcg ccatgactct tgccgtggtt    1020
gccctatttg ctgatggccc aactgctatc agagatgtgg cttcctggag agtaaaggag    1080
accgagagga tggttgcaat ccggactgag ctaacaaagc tgggagcgtc ggtcgaggaa    1140
ggactggact actgcattat cacaccgccc gagaagctga acgtaacggc catcgacacc    1200
tacgatgacc acaggatggc catgccttc tccctcgccg cctgcgccga cgtgcctgtg    1260
accatccggg accccggctg cacccgcaag accttcccag actacttcga cgtgctgagc    1320
```

```
                                       actttcgtca agaactaa                                        1338

<210> SEQ ID NO 7
<211> LENGTH: 445
<212> TYPE: PRT
<213> ORGANISM: Eleusine indica

<400> SEQUENCE: 7

Ala Gly Ala Glu Glu Val Val Leu Gln Pro Ile Lys Glu Ile Ser Gly
  1               5                  10                  15

Val Val Lys Leu Pro Gly Ser Lys Ser Leu Ser Asn Arg Ile Leu Leu
             20                  25                  30

Leu Ser Ala Leu Ala Glu Gly Thr Thr Val Val Asp Asn Leu Leu Asn
         35                  40                  45

Ser Glu Asp Val His Tyr Met Leu Gly Ala Leu Lys Thr Leu Gly Leu
 50                  55                  60

Ser Val Glu Ala Asp Lys Ala Ala Lys Arg Ala Val Val Val Gly Cys
 65                  70                  75                  80

Gly Gly Lys Phe Pro Val Glu Lys Asp Ala Lys Glu Glu Val Gln Leu
                 85                  90                  95

Phe Leu Gly Asn Ala Gly Thr Ala Met Arg Ser Leu Thr Ala Ala Val
                100                 105                 110

Thr Ala Ala Gly Gly Asn Ala Thr Tyr Val Leu Asp Gly Val Pro Arg
            115                 120                 125

Met Arg Glu Arg Pro Ile Gly Asp Leu Val Val Gly Leu Lys Gln Leu
130                 135                 140

Gly Ala Asp Val Asp Cys Phe Leu Gly Thr Asp Cys Pro Pro Val Arg
145                 150                 155                 160

Val Lys Gly Ile Gly Gly Leu Pro Gly Gly Lys Val Lys Leu Ser Gly
                165                 170                 175

Ser Ile Ser Ser Gln Tyr Leu Ser Ala Leu Leu Met Ala Ala Pro Leu
            180                 185                 190

Ala Leu Gly Asp Val Glu Ile Glu Ile Ile Asp Lys Leu Ile Ser Ile
        195                 200                 205

Pro Tyr Val Glu Met Thr Leu Arg Leu Met Glu Arg Phe Gly Val Lys
210                 215                 220

Ala Glu His Ser Asp Ser Trp Asp Arg Phe Tyr Ile Lys Gly Gly Gln
225                 230                 235                 240

Lys Tyr Lys Ser Pro Lys Asn Ala Tyr Val Glu Gly Asp Ala Ser Ser
                245                 250                 255

Ala Ser Tyr Phe Leu Ala Gly Ala Ala Ile Thr Gly Gly Thr Val Thr
            260                 265                 270

Val Glu Gly Cys Gly Thr Thr Ser Leu Gln Gly Asp Val Lys Phe Ala
        275                 280                 285

Glu Val Leu Glu Met Met Gly Ala Lys Val Thr Trp Thr Glu Thr Ser
    290                 295                 300

Val Thr Val Thr Gly Pro Gln Arg Glu Pro Phe Gly Arg Lys His Leu
305                 310                 315                 320

Lys Ala Ile Asp Val Asn Met Asn Lys Met Pro Asp Val Ala Met Thr
                325                 330                 335

Leu Ala Val Val Ala Leu Phe Ala Asp Gly Pro Thr Ala Ile Arg Asp
            340                 345                 350

Val Ala Ser Trp Arg Val Lys Glu Thr Glu Arg Met Val Ala Ile Arg
        355                 360                 365
```

```
Thr Glu Leu Thr Lys Leu Gly Ala Ser Val Glu Gly Leu Asp Tyr
    370                 375                 380

Cys Ile Ile Thr Pro Pro Glu Lys Leu Asn Val Thr Ala Ile Asp Thr
385                 390                 395                 400

Tyr Asp Asp His Arg Met Ala Met Ala Phe Ser Leu Ala Ala Cys Ala
                405                 410                 415

Asp Val Pro Val Thr Ile Arg Asp Pro Gly Cys Thr Arg Lys Thr Phe
            420                 425                 430

Pro Asp Tyr Phe Asp Val Leu Ser Thr Phe Val Lys Asn
        435                 440                 445

<210> SEQ ID NO 8
<211> LENGTH: 56
<212> TYPE: DNA
<213> ORGANISM: Artificial sequence
<220> FEATURE:
<221> NAME/KEY: 5'UTR
<222> LOCATION: (1)..(56)
<223> OTHER INFORMATION: fully synthetic DNA leader sequence

<400> SEQUENCE: 8
agatctccta gggcttaatt aattaagcac tagtcacaca ggaggtaatt catatg      56

<210> SEQ ID NO 9
<211> LENGTH: 36
<212> TYPE: DNA
<213> ORGANISM: Artificial sequence
<220> FEATURE:
<221> NAME/KEY: exon
<222> LOCATION: (1)..(36)
<223> OTHER INFORMATION: fully synthetic DNA sequence

<400> SEQUENCE: 9 gca att cca tat ggc ggg cgc gga gga ggt ggt gct                    36
Ala Ile Pro Tyr Gly Gly Arg Gly Gly Gly Gly Ala
1               5                   10

<210> SEQ ID NO 10
<211> LENGTH: 48
<212> TYPE: DNA
<213> ORGANISM: Artificial sequence
<220> FEATURE:
<221> NAME/KEY: exon
<222> LOCATION: (1)..(48)
<223> OTHER INFORMATION: fully synthetic DNA sequence

<400> SEQUENCE: 10 gac tag gaa ttc tta gtt ctt ttg acg aaa gtg ctc agc acg tcg aag    48
Asp     Glu Phe Leu Val Leu Leu Thr Lys Val Leu Ser Thr Ser Lys
1               5                   10                  15

<210> SEQ ID NO 11
<211> LENGTH: 35
<212> TYPE: DNA
<213> ORGANISM: Artificial sequence
<220> FEATURE:
<221> NAME/KEY: exon
<222> LOCATION: (1)..(35)
<223> OTHER INFORMATION: fully synthetic DNA sequence

<400> SEQUENCE: 11 gca att cgc atg ccg ggc gcg gag gag gtg gtg ct                     35
Ala Ile Arg Met Pro Gly Ala Glu Glu Val Val
1               5                   10

<210> SEQ ID NO 12
```

-continued

```
<211> LENGTH: 48
<212> TYPE: DNA
<213> ORGANISM: Artificial sequence
<220> FEATURE:
<221> NAME/KEY: exon
<222> LOCATION: (1)..(48)
<223> OTHER INFORMATION: fully synthetic DNA sequence

<400> SEQUENCE: 12 gac tag gaa ttc tta gtt ctt ttg acg aaa gtg ctc agc acg tcg aag        48
Asp  Glu Phe Leu Val Leu Leu Thr Lys Val Leu Ser Thr Ser Lys
1              5                  10                  15

<210> SEQ ID NO 13
<211> LENGTH: 26
<212> TYPE: DNA
<213> ORGANISM: Artificial sequence
<220> FEATURE:
<221> NAME/KEY: exon
<222> LOCATION: (1)..(26)
<223> OTHER INFORMATION: fully synthetic DNA sequence

<400> SEQUENCE: 13 tgc aat ccg gac tga gct aac aaa gc                                     26
Cys Asn Pro Asp     Ala Asn Lys
1               5

<210> SEQ ID NO 14
<211> LENGTH: 26
<212> TYPE: DNA
<213> ORGANISM: Artificial sequence
<220> FEATURE:
<221> NAME/KEY: exon
<222> LOCATION: (1)..(26)
<223> OTHER INFORMATION: fully synthetic DNA sequence

<400> SEQUENCE: 14 act gca tta tca cac cgc ccg aga ag                                     26
Thr Ala Leu Ser His Arg Pro Arg
1               5

<210> SEQ ID NO 15
<211> LENGTH: 36
<212> TYPE: DNA
<213> ORGANISM: Artificial sequence
<220> FEATURE:
<221> NAME/KEY: exon
<222> LOCATION: (1)..(36)
<223> OTHER INFORMATION: fully synthetic DNA sequence

<400> SEQUENCE: 15 cta agg atc ctc tgt gcc tgc ctc atg aag aga gtt                        36
Leu Arg Ile Leu Cys Ala Cys Leu Met Lys Arg Val
1               5                   10

<210> SEQ ID NO 16
<211> LENGTH: 36
<212> TYPE: DNA
<213> ORGANISM: Artificial sequence
<220> FEATURE:
<221> NAME/KEY: exon
<222> LOCATION: (1)..(36)
<223> OTHER INFORMATION: fully synthetic DNA sequence

<400> SEQUENCE: 16 tga tct gca ggc aag tgt ctt acc ctt acc ctt ctg                        36
    Ser Ala Gly Lys Cys Leu Thr Leu Thr Leu Leu
1               5                   10
```

METHODS FOR MAKING PLANTS TOLERANT TO GLYPHOSATE AND COMPOSITIONS THEREOF USING A DNA ENCODING AN EPSPS ENZYME FROM *ELEUSINE INDICA*

This application claims priority from U.S. Provisional Application 60/188,093, filed Mar. 9, 2000.

FIELD OF THE INVENTION

This invention relates in general to plant molecular biology and plant genetic engineering for herbicide resistance and, more particularly, to a novel glyphosate resistant 5-enolpyruvylshikimate-3-phosphate synthase from *Eleusine indica*. Plant genetic engineering methods can be used to transfer the glyphosate resistant 5-enolpyruvylshikimate-3-phosphate synthase gene isolated and purified from *Eleusine indica* into crop and ornamental plants of economic importance.

BACKGROUND OF THE INVENTION

N-phosphonomethylglycine, also known as glyphosate, is a well known herbicide that has activity on a broad spectrum of plant species. Glyphosate is the active ingredient of Roundup® (Monsanto Co.), a safe herbicide having a desirably short half life in the environment. When applied onto a plant surface, glyphosate moves systemically through the plant. Glyphosate is toxic to plants by inhibiting the shikimic acid pathway that provides a precursor for the synthesis of aromatic amino acids. Specifically, glyphosate affects the conversion of phosphoenolpyruvate and 3-phosphoshikimic acid to 5-enolpyruvyl-3-phosphoshikimic acid by inhibiting the enzyme 5-enolpyruvyl-3-phosphoshikimate synthase (hereinafter referred to as EPSP synthase or EPSPS). For purposes of the present invention, the term "glyphosate" should be considered to include any herbicidally effective form of N-phosphonomethylglycine (including any salt thereof) and other forms that result in the production of the glyphosate anion in planta.

Through plant genetic engineering methods, it is possible to produce glyphosate tolerant plants by inserting into the plant genome a DNA molecule that causes the production of higher levels of wild-type EPSPS (Shah et al., Science 233:478–481 (1986). Glyphosate tolerance can also be achieved by the expression of EPSPS variants that have lower affinity for glyphosate and therefore retain their catalytic activity in the presence of glyphosate (U.S. Pat. No. 4,940,835, U.S. Pat. No. 5,094,945, U.S. Pat. No. 5,633,435). Enzymes that degrade glyphosate in the plant tissues (U.S. Pat. No. 5,463,175) are also capable of conferring cellular tolerance to glyphosate. Such genes, therefore, allow for the production of transgenic crops that are tolerant to glyphosate, thereby allowing glyphosate to be used for effective weed control with minimal concern of crop damage. For example, glyphosate tolerance has been genetically engineered into corn (U.S. Pat. No. 5,554,798), wheat (Zhou et al. Plant Cell Rep. 15:159–163 (1995), soybean (WO 9200377) and canola (WO 9204449).

Variants of the wild-type EPSPS enzyme are glyphosate-resistant as a result of alterations in the EPSPS amino acid coding sequence (Kishore et al., Annu. Rev. Biochem. 57:627–663 (1988); Schulz et al., Arch. Microbiol. 137:121–123 (1984); Sost et al., FEBS Lett. 173:238–241 (1984); Kishore et al., In "Biotechnology for Crop Protection" ACS Symposium Series No. 379. Eds. Hedlin et al., 37–48 (1988). These variants typically have a higher $K_i$ for glyphosate than the wild-type EPSPS enzyme that confers the glyphosate-tolerant phenotype, but these variants are also characterized by a high $K_m$ for PEP that makes the enzyme kinetically less efficient. For example, the apparent $K_m$ for PEP and the apparent $K_i$ for glyphosate for the native EPSPS from *E. coli* are 10 $\mu$M and 0.5 $\mu$M while for a glyphosate-resistant isolate having a single amino acid substitution of an alanine for the glycine at position 96 these values are 220 $\mu$M and 4.0 mM, respectively. A number of glyphosate-resistant plant variant EPSPS genes have been constructed by mutagenesis.

A variety of native and variant EPSPS enzymes have been expressed in transgenic plants in order to confer glyphosate tolerance (Singh, et al., In "Biosynthesis and Molecular Regulation of Amino Acids in Plants", Amer Soc Plant Phys. Pubs (1992). Examples of some of these EPSP Synthases and methods for preparing transgenic plants resistant to glyphosate include those described and/or isolated in accordance with U.S. Pat. Nos. 4,940,835, 4,971,908, 5,145,783, 5,188,642, 5,310,667, 5,312,910, and 6,40,497. They can also be derived from a structurally distinct class of non-homologous EPSPS genes, such as the naturally occurring class II EPSPS genes isolated from Agrobacterium sp. strain CP4 as described in U.S. Pat. No. 5,633,435 and U.S. Pat. No. 5,627,061.

*Eleusine indica* is commonly referred to as "goose grass" and may also be known as "yard grass". It is a common monocotyledonous plant found world wide. As a member of the Poaceae family, the grass family, it is related to many well known crop plants. *Eleusine indica* is most closely related to the millets, that include *Sorghum bicolor* (sorghum or great millet), *Zea mays* (maize), *Pennisetum americanum* (pearl millet), *Eleusine coracana* (finger millet), *Setaria italica* (foxtail millet), *Paspalum scrobiculatum* (kodo millet), *Echinochloa frumentacea* (barnyhard millet) and *Eragrostis tef* (teff) (Chennaveeraiah et al., In "Chromosome engineering in plants: genetics, breeding and evolution", Cytogenetics of Minor Millets, in Tsuchiya et al., eds Elsevier Sci Pub Amsterdam, 613–627 (1991). *Eleusine indica* has been shown to hybridize with *Eleusine coracana* (finger millet), an important cultivated millet of India and East Africa (Chennaveeraiah et al., Euphytica 2–3:489–495, (1974). Classical plant breeding methods can be used to transfer the genes and traits of interest from *Eleusine indica* into agronomic crop plants within the family Poaceae.

SUMMARY OF THE INVENTION

In its broadest sense, the present invention herein provides a method for plant tolerance to glyphosate herbicide by the expression of an isolated DNA molecule encoding a naturally occurring glyphosate resistant EPSPS enzyme. The enzyme and the DNA is isolated from Eleusine species, more particularly *Eleusine indica* (*E. indica*).

In the first aspect of the present invention described herein provides a method to cause plants to be tolerant to glyphosate herbicide by the insertion of a recombinant DNA molecule into the nuclear genome of a plant cell, the recombinant DNA molecule comprising:

a promoter that functions in plant cells to cause the production of an RNA molecule; operably linked to, a DNA molecule transcribing an RNA encoding for a chloroplast transit peptide and a *E. indica* glyphosate resistant EPSPS enzyme; operably linked to, a 3' non-translated region that functions in plant cells to cause the polyadenylation of the 3' end of the RNA molecule.

Typically, the promoter used in the DNA molecule is expressed in a constitutive fashion. Examples of suitable promoters that function effectively in this capacity include cauliflower mosaic virus 19S promoter, cauliflower mosaic virus 35S promoter, figwort mosaic virus 34S promoter, sugarcane bacilliform virus promoter, commelina yellow mottle virus promoter, small subunit of ribulose-1,5-bisphosphate carboxylase promoter, rice cytosolic triose-phosphate isomerase promoter, adenine phosphoribosyl-transferae promoter, rice actin 1 promoter, maize ubiquitin promoter, mannopine synthase promoter and octopine synthase promoter. A Promoter may also comprise leader sequences and intron sequences useful in the invention.

A DNA molecule that encodes a chloroplast transit peptide sequence can be isolated from EPSPS genes purified from various plant species including *E. indica* as well as from various plant genes whose protein products have been shown to be transported into the chloroplast.

A DNA molecule that encodes a glyphosate resistant EPSPS enzyme isolated from Eleusine species, more particularly from *E. indica*, comprising SEQ ID NO:7 is an object of the invention and a DNA molecule substantially homologous to the DNA molecule isolated from *E. indica* or a portion thereof identified as SEQ ID NO:6.

The 3' non-translated region can be obtained from various genes that are expressed in plant cells. The nopaline synthase 3' untranslated, the 3' untranslated region from pea small subunit Rubisco gene, the wheat heat shock protein 17.9 3' untranslated region, the 3' untranslated region from soybean 7S seed storage protein gene are commonly used in this capacity.

The invention also relates to a glyphosate tolerant transgenic crop plant cell, a glyphosate tolerant crop plant and crop plant parts, crop seeds and progeny thereof comprising the recombinant DNA molecule of the present invention.

A DNA molecule that encodes a naturally occurring plant derived glyphosate resistant EPSPS enzyme, wherein the glyphosate resistant EPSPS enzyme has a $K_m$ for phosphoenolpyruvate (PEP) of less than 10 $\mu$M. More preferably, a DNA molecule that encodes a naturally occurring plant derived glyphosate resistant EPSPS enzyme wherein the glyphosate resistant EPSPS enzyme has a $K_m$ for PEP of less than 10 $\mu$M and the $K_m$ for PEP is not more than about 2× of the naturally occurring plant derived glyphosate sensitive EPSPS enzyme.

A DNA molecule that encodes a naturally occurring glyphosate resistant EPSPS enzyme derived from Eleusine species, wherein the glyphosate resistant EPSPS enzyme has a $K_m$ for phosphoenolpyruvate (PEP) of less than 10 $\mu$M. More preferably, a DNA molecule that encodes a naturally occurring glyphosate resistant EPSPS enzyme derived from Eleusine species, wherein the glyphosate resistant EPSPS enzyme has a $K_m$ for PEP of less than 10 $\mu$M and the $K_m$ for PEP is not more than about 2× of the naturally occurring plant derived glyphosate sensitive EPSPS enzyme.

A DNA molecule that encodes a naturally occurring glyphosate resistant EPSPS enzyme derived from *E. indica*, wherein the naturally occurring glyphosate resistant EPSPS enzyme amino acid sequence has been modified by amino acid substitutions selected from the group consisting of threonine to isoleucine at amino acid position 103 and glycine to alanine at amino acid position 102.

The invention also relates to the homologous genetic elements regulating expression of the *E. indica* glyphosate resistant EPSPS gene. These elements include but are not limited to the DNA sequences of a promoter, a 5' untranslated region, a chloroplast transit peptide, an intron, and a 3' untranslated region of *E. indica* EPSPS glyphosate resistance gene. A DNA molecule that encodes a glyphosate resistant EPSPS enzyme purified from the genome of Eleusine species, more particularly from *E. indica* glyphosate resistant biotype provided by the ATCC deposit #PTA-2177 is an object of the invention.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1. *Eleusine indica* (glypho sate tolerant) EPSP synthase DNA sequence (SEQ ID NO:6).

FIG. 2. Deduced amino acid sequence for the mature protein-coding region of the *Eleusine indica* (glyphosate tolerant biotype) EPSP synthase gene (SEQ ID NO:7).

FIG. 9. The amino acid sequence deduced from the cDNA sequence of the mature EPSP synthase protein sequence derived from the glyphosate-tolerant *E. indica* biotype (top row) aligned with that of the glyphosate sensitive *E. indica* biotype (bottom row).

DETAILED DESCRIPTION OF THE INVENTION

Figure 3A:
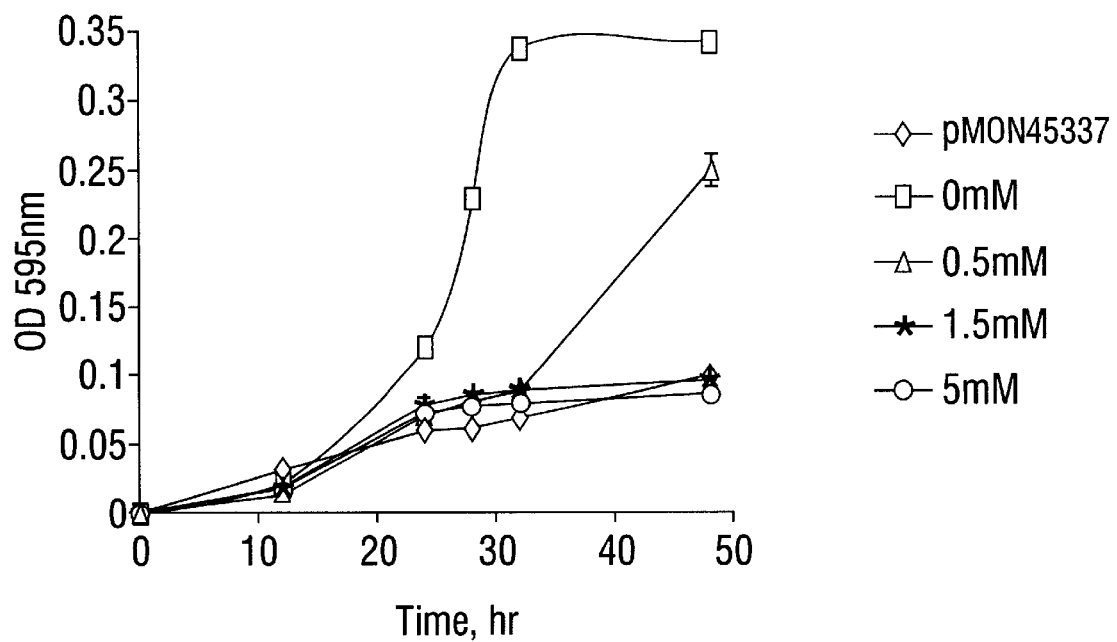
FIG. 3. Growth rates on glyphosate containing media of transgenic *E. coli* on expressing the *E. indica* glyphosate sensitive EPSPS enzyme and the *E. indica* glyphosate resistant EPSPS enzyme.

The following definitions and methods are provided to better define the present invention and to guide those of ordinary skill in the art in the practice of the present invention. Unless otherwise noted, terms are to be understood according to conventional usage by those of ordinary skill in the relevant art. Definitions of common terms in molecular biology may also be found in Rieger et al., Glossary of Genetics: Classical and Molecular, 5th edition, Springer-Verlag: New York, (1991); and Lewin, Genes V, Oxford University Press: New York, (1994). The nomenclature for DNA bases as set forth at 37 CFR §1.822 is used. The standard one- and three-letter nomenclature for amino acid residues is used.

"cDNA library" refers to a collection of cDNA fragments, each cloned into a separate vector molecule.

The term "chimeric" refers to a fusion nucleic acid or protein sequence. A chimeric nucleic acid coding sequence is comprised of two or more sequences joined in-frame that encode a chimeric protein. A chimeric gene refers to the multiple genetic elements derived from heterologous sources comprising a gene.

The phrases "coding sequence", "open reading frame", and "structural sequence" refer to the region of continuous sequential nucleic acid triplets encoding a protein, polypeptide, or peptide sequence.

"Codon" refers to a sequence of three nucleotides that specify a particular amino acid.

"Complementarity" and "complement" when referring to nucleic acid sequences, refers to the specific binding of adenine to thymine (or uracil in RNA) and cytosine to guanine on opposite strands of DNA or RNA.

"Construct" refers to the heterologous genetic elements operably linked to each other making up a recombinant DNA molecule.

"C-terminal region" refers to the region of a peptide, polypeptide, or protein chain from the middle thereof to the end that carries the amino acid having a free carboxyl group.

The term "encoding DNA" refers to chromosomal DNA, plasmid DNA, cDNA, or synthetic DNA that encodes any of the proteins discussed herein.

The term "endogenous" refers to materials originating from within an organism or cell.

"Endonuclease" refers to an enzyme that hydrolyzes double stranded DNA at internal locations.

"Exogenous" refers to materials originating from outside of an organism or cell. This typically applies to nucleic acid molecules used in producing transformed or transgenic host cells and plants.

"Exon" refers to the portion of a gene that is actually translated into protein, i.e. a coding sequence.

The term "expression" refers to the transcription of a gene to produce the corresponding mRNA.

"Fragments". A fragment of a EPSPS gene is a portion of a full-length EPSPS gene nucleic acid that is of at least a minimum length capable of expressing a protein with EPSPS activity.

The term "gene" refers to chromosomal DNA, plasmid DNA, cDNA, synthetic DNA, or other DNA that encodes a peptide, polypeptide, protein, or RNA molecule, and regions flanking the coding sequence involved in the regulation of expression.

The term "genome" as it applies to viruses encompasses all of the nucleic acid sequence contained within the capsid of the virus. The term "genome" as it applies to bacteria encompasses both the chromosome and plasmids within a bacterial host cell. Encoding nucleic acids of the present invention introduced into bacterial host cells can therefore be either chromosomally-integrated or plasmid-localized. The term "genome" as it applies to plant cells encompasses not only chromosomal DNA found within the nucleus, but organelle DNA found within subcellular components of the cell. Nucleic acids of the present invention introduced into plant cells can therefore be either chromosomally-integrated or organelle-localized.

"Glyphosate" refers to N-phosphonomethylglycine and its' salts, Glyphosate is the active ingredient of Roundup® herbicide (Monsanto Co.). Plant treatments with "glyphosate" refer to treatments with the Roundup® or Roundup Ultra® herbicide formulation, unless otherwise stated. Glyphosate as N-phosphonomethylglycine and its' salts (not formulated Roundup® herbicide) are components of synthetic culture media used for the selection of bacteria and plant tolerance to glyphosate or used to determine enzyme resistance in in vitro biochemical assays.

"Heterologous DNA" refers to DNA from a source different than that of the recipient cell.

"Homologous DNA" refers to DNA from the same source as that of the recipient cell.

"Hybridization" refers to the ability of a strand of nucleic acid to join with a complementary strand via base pairing. Hybridization occurs when complementary sequences in the two nucleic acid strands bind to one another.

"Identity" refers to the degree of similarity between two nucleic acid or protein sequences. An alignment of the two sequences is performed by a suitable computer program. A widely used and accepted computer program for performing sequence alignments is CLUSTALW v1.6 (Thompson, et al. Nucl. Acids Res., 22: 4673–4680, 1994). The number of matching bases or amino acids is divided by the total number of bases or amino acids, and multiplied by 100 to obtain a percent identity. For example, if two 580 base pair sequences had 145 matched bases, they would be 25 percent identical. If the two compared sequences are of different lengths, the number of matches is divided by the shorter of the two lengths. For example, if there are 100 matched amino acids between 200 and a 400 amino acid proteins, they are 50 percent identical with respect to the shorter sequence. If the shorter sequence is less than 150 bases or 50 amino acids in length, the number of matches are divided by 150 (for nucleic acid bases) or 50 (for amino acids), and multiplied by 100 to obtain a percent identity.

"Intron" refers to a portion of a gene not translated into protein, even though it is transcribed into RNA.

"Isolated" An "isolated" nucleic acid is one that has been substantially separated or purified away from other nucleic acid sequences in the cell of the organism that the nucleic acid naturally occurs, i.e., other chromosomal and extrachromosomal DNA and RNA, by conventional nucleic acid-purification methods. The term also embraces recombinant nucleic acids and chemically synthesized nucleic acids.

"Native" The term "native" refers to a naturally-occurring ("wild-type") nucleic acid or polypeptide.

"N-terminal region" refers to the region of a peptide, polypeptide, or protein chain from the amino acid having a free amino group to the middle of the chain.

"Nucleic acid" refers to deoxyribonucleic acid (DNA) and ribonucleic acid (RNA).

Nucleic acid codes: A=adenosine; C=cytosine; G=guanosine; T=thymidine. Codes used for synthesis of oligonucleotides: N=equimolar A, C, G, and T; I=deoxyinosine; K=equimolar G and T; R=equimolar A and G; S=equimolar C and G; W=equimolar A and T; Y=equimolar C and T.

A "nucleic acid segment" or a "nucleic acid molecule segment" is a nucleic acid molecule that has been isolated free of total genomic DNA of a particular species, or that has been synthesized. Included with the term "nucleic acid segment" are DNA segments, recombinant vectors, plasmids, cosmids, phagemids, phage, viruses, et cetera.

"Nucleic-Acid Hybridization"; "Stringent Conditions"; "Specific" The term "stringent conditions" is functionally defined with regard to the hybridization of a nucleic-acid probe to a target nucleic acid (i.e., to a particular nucleic-acid sequence of interest) by the specific hybridization procedure discussed in Sambrook et al., *Molecular Cloning: A Laboratory Manual,* Cold Spring Harbor Press (1989), at 9.52–9.55. See also, Sambrook et al., *Molecular Cloning: A Laboratory Manual,* Cold Spring Harbor Press (1989) at 9.47–9.52, 9.56–9.58; Kanehisa, Nucl. Acids Res. 12:203–213, (1984); and Wetmur and Davidson, J. Mol. Biol. 31:349–370, (1968).

"Nucleotide Sequence Variants" Using well-known methods, the skilled artisan can readily produce nucleotide and amino acid sequence variants of EPSPS genes and proteins, respectively. "Variant" DNA molecules are DNA molecules containing minor changes in a native EPSPS gene sequence, i.e., changes that one or more nucleotides of a native EPSPS gene sequence is deleted, added, and/or substituted, such that the variant EPSPS gene encodes a protein that retains EPSPS activity. Variant DNA molecules can be produced, for example, by standard DNA mutagenesis techniques or by chemically synthesizing the variant DNA molecule or a portion thereof. Methods for chemical synthesis of nucleic acids are discussed, for example, in Beaucage et al., Tetra. Letts. 22:1859–1862 (1981), and Matteucci et al., J. Am. Chem. Soc. 103:3185- (1981). Chemical synthesis of nucleic acids can be performed, for example, on automated oligonucleotide synthesizers. Such variants preferably do not change the reading frame of the protein-coding region of the nucleic acid and preferably encode a protein having no amino acid changes. Nucleic acid sequence variants are most often created for the purposes of modification of the sequence to add or delete restriction endonuclease sites or to affect transcription or translation of the nucleic acid molecule.

"Amino-acid substitutions", "Amino-acid variants", are preferably substitutions of single amino-acid residue for another amino-acid residue at any position within the protein. Substitutions, deletions, insertions or any combination thereof can be combined to arrive at a final construct.

"Open reading frame (ORF)" refers to a region of DNA or RNA encoding a peptide, polypeptide, or protein.

"Operably Linked". A first nucleic-acid sequence is "operably" linked with a second nucleic-acid sequence when the first nucleic-acid sequence is placed in a functional relationship with the second nucleic-acid sequence. For instance, a promoter is operably linked to a protein-coding sequence if the promoter effects the transcription or expression of the coding sequence. Generally, operably linked DNA sequences are contiguous and, where necessary to join two protein-coding regions, in reading frame.

"Overexpression" refers to the expression of a polypeptide or protein encoded by a DNA introduced into a host cell, wherein said polypeptide or protein is either not normally present in the host cell, or wherein said polypeptide or protein is present in said host cell at a higher level than that normally expressed from the endogenous gene encoding said polypeptide or protein.

"Plant expression vector" refers to chimeric DNA molecules comprising the regulatory elements that are operably linked to provide the expression of a transgene product in plants.

"Plasmid" refers to a circular, extrachromosomal, self-replicating piece of DNA.

"Polyadenylation signal" or "polyA signal" refers to a nucleic acid sequence located 3' to a coding region that causes the addition of adenylate nucleotides to the 3' end of the mRNA transcribed from the coding region.

"Polymerase chain reaction (PCR)" refers to an enzymatic technique to create multiple copies of one sequence of nucleic acid. Copies of DNA sequence are prepared by shuttling a DNA polymerase between two amplimers. The basis of this amplification method is multiple cycles of temperature changes to denature, then re-anneal amplimers, followed by extension to synthesize new DNA strands in the region located between the flanking amplimers.

The term "promoter" or "promoter region" refers to a nucleic acid sequence, usually found upstream (5') to a coding sequence, that controls expression of the coding sequence by controlling production of messenger RNA (mRNA) by providing the recognition site for RNA polymerase and/or other factors necessary for start of transcription at the correct site. As contemplated herein, a promoter or promoter region includes variations of promoters derived by means of ligation to various regulatory sequences, random or controlled mutagenesis, and addition or duplication of enhancer sequences. The promoter region disclosed herein, and biologically functional equivalents thereof, are responsible for driving the transcription of coding sequences under their control when introduced into a host as part of a suitable recombinant vector, as demonstrated by its ability to produce mRNA.

"Recombinant". A "recombinant" nucleic acid is made by an artificial combination of two otherwise separated segments of sequence, e.g., by chemical synthesis or by the manipulation of isolated segments of nucleic acids by genetic engineering techniques.

The term "recombinant DNA construct" or "recombinant vector" refers to any agent such as a plasmid, cosmid, virus, autonomously replicating sequence, phage, or linear or circular single-stranded or double-stranded DNA or RNA nucleotide sequence, derived from any source, capable of genomic integration or autonomous replication, comprising a DNA molecule that one or more DNA sequences have been linked in a functionally operative manner. Such recombinant DNA constructs or vectors are capable of introducing a 5' regulatory sequence or promoter region and a DNA sequence for a selected gene product into a cell in such a manner that the DNA sequence is transcribed into a functional mRNA that is translated and therefore expressed. Recombinant DNA constructs or recombinant vectors may be constructed to be capable of expressing antisense RNAs, in order to inhibit translation of a specific RNA of interest.

"Regeneration" refers to the process of growing a plant from a plant cell (e.g., plant protoplast or explant).

"Reporter" refers to a gene and corresponding gene product that when expressed in transgenic organisms produces a product detectable by chemical or molecular methods or produces an observable phenotype.

"Restriction enzyme" refers to an enzyme that recognizes a specific palindromic sequence of nucleotides in double stranded DNA and cleaves both strands; also called a restriction endonuclease. Cleavage typically occurs within the restriction site.

"Selectable marker" refers to a nucleic acid sequence whose expression confers a phenotype facilitating identification of cells containing the nucleic acid sequence. Selectable markers include those that confer resistance to toxic chemicals (e.g. ampicillin resistance, kanamycin resistance), complement a nutritional deficiency (e.g. uracil, histidine, leucine), or impart a visually distinguishing characteristic (e.g. color changes or fluorescence). Useful dominant selectable marker genes include genes encoding antibiotic resistance genes (e.g., resistance to hygromycin, kanamycin, bleomycin, G418, streptomycin or spectinomycin); and herbicide resistance genes (e.g., phosphinothricin acetyltransferase). A useful strategy for selection of transformants for herbicide resistance is described, e.g., in Vasil, Cell Culture and Somatic Cell Genetics of Plants, Vols. I–III, Laboratory Procedures and Their Applications Academic Press, New York (1984).

The term "specific for (a target sequence)" indicates that a probe or primer hybridizes under given hybridization conditions only to the target sequence in a sample comprising the target sequence.

"Tolerant" refers to a reduced toxic effect of glyphosate on the growth and development of microorganisms and plants.

"Transcription" refers to the process of producing an RNA copy from a DNA template.

"Transformation" refers to a process of introducing an exogenous nucleic acid sequence (e.g., a vector, recombinant nucleic acid molecule) into a cell or protoplast that exogenous nucleic acid is incorporated into a chromosome or is capable of autonomous replication.

"Transformed" or "transgenic" refers to a cell, tissue, organ, or organism into that has been introduced a foreign nucleic acid, such as a recombinant vector. A "transgenic" or "transformed" cell or organism also includes progeny of the cell or organism and progeny produced from a breeding program employing such a "transgenic" plant as a parent in a cross and exhibiting an altered phenotype resulting from the presence of the foreign nucleic acid.

The term "transgene" refers to any nucleic acid sequence normative to a cell or organism transformed into said cell or organism. "Transgene" also encompasses the component parts of a native plant gene modified by insertion of a normative nucleic acid sequence by directed recombination.

The term "translation" refers to the production the corresponding gene product, i.e., a peptide, polypeptide, or protein from a mRNA.

"Vector" refers to a plasmid, cosmid, bacteriophage, or virus that carries foreign DNA into a host organism.

"Isolated," "Purified," "Homogeneous" Polypeptides. A polypeptide is "isolated" if it has been separated from the cellular components (nucleic acids, lipids, carbohydrates, and other polypeptides) that naturally accompany it or that is chemically synthesized or recombinant. A monomeric polypeptide is isolated when at least 60% by weight of a sample is composed of the polypeptide, preferably 90% or more, more preferably 95% or more, and most preferably more than 99%. Protein purity or homogeneity is indicated, for example, by polyacrylamide gel electrophoresis of a protein sample, followed by visualization of a single polypeptide band upon staining the polyacrylamide gel; high pressure liquid chromatography; or other conventional methods. Coat proteins can be purified by any of the means known in the art, for example as described in Guide to Protein Purification, ed. Deutscher, Meth. Enzymol. 185, Academic Press, San Diego, 1990; and Scopes, Protein Purification: Principles and Practice, Springer Verlag, New York, 1982.

"Labeling". There are a variety of conventional methods and reagents for labeling polypeptides and fragments thereof. Typical labels include radioactive isotopes, ligands or ligand receptors, fluorophores, chemiluminescent agents, and enzymes. Methods for labeling and guidance in the choice of labels appropriate for various purposes are discussed, e.g., in Sambrook et al., *Molecular Cloning: A Laboratory Manual,* Cold Spring Harbor Press (1989) and Ausubel et al., Greene Publishing and Wiley-Interscience, New York, (1992).

"Mature protein coding region". This term refers to the sequence of the processed protein product of EPSPS remaining after the chloroplast transit peptide sequence has been removed.

"Polypeptide fragments". The present invention also encompasses fragments of an *E indica* EPSPS that lacks at least one residue of a native full-length *E. indica* EPSPS protein, but that specifically maintains EPSPS activity.

"Transit peptide or targeting peptide sequence". These terms generally refer to peptide sequences that when linked to a protein of interest directs the protein to a particular tissue, cell, subcellular location, or cell organelle. Examples include, but are not limited to, chloroplast transit peptides, nuclear targeting signals, and vacuolar signals. The chloroplast transit peptide is of particular utility in the present invention to direct expression of the EPSPS enzyme to the chloroplast.

The term "plant" encompasses any higher plant and progeny thereof, including monocots (e.g., corn, rice, wheat, barley, etc.), dicots (e.g., soybean, cotton, tomato, potato, Arabidopsis, tobacco, etc.), gymnosperms (pines, firs, cedars, etc) and includes parts of plants, including reproductive units of a plant (e.g., seeds, bulbs, tubers, or other parts or tissues from that the plant can be reproduced), fruits and flowers.

Exogenous genetic material may be transferred into a plant by the use of a DNA vector designed for such a purpose by methods that utilize Agrobacterium, particle bombardment or other methods known to those skilled in the art. A particularly preferred subgroup of exogenous material comprises a nucleic acid molecule of the present invention. Design of such a vector is generally within the skill of the art (Plant Molecular Biology: A Laboratory Manual, eds. Clark, Springer, New York (1997). Examples of such plants in to which exogenous genetic material may be transferred, include, without limitation, alfalfa, Arabidopsis, barley, Brassica, broccoli, cabbage, citrus, cotton, garlic, oat, oilseed rape, onion, canola, flax, maize, an ornamental annual and ornamental perennial plant, pea, peanut, pepper, potato, rice, rye, sorghum, soybean, strawberry, sugarcane, sugar beet, tomato, wheat, poplar, pine, fir, eucalyptus, apple, lettuce, lentils, grape, banana, tea, turf grasses, sunflower, oil palm, Phaseolus etc.

The particular promoters selected for use in embodiments of the present invention should be capable of causing the production of sufficient expression to, in the case of the DNA molecule, generate protein expression in vegetative and reproductive tissues of a transformed plant. The DNA molecule will typically contain a constitutive promoter, a structural DNA sequence encoding a herbicide resistant enzyme, and a 3' non-translated region. A number of constitutive promoters that are active in plant cells have been described. Suitable promoters for constitutive expression in plants of herbicide tolerance for the DNA molecule include, but are not limited to, the cauliflower mosaic virus (CaMV) 35S promoter (Odell et al. Nature 313:801–812 (1985), the Figwort mosaic virus (FMV) 35S (Sanger et al. Plant Mol. Biol. 14:433–443 (1990), the sugarcane bacilliform virus promoter (Bouhida et al., J. Gen. Virol. 74:15–22 (1993), the commelina yellow mottle virus promoter (Medberry et al., Plant J. 3:619–626 (1993), the light-inducible promoter from the small subunit of the ribulose-1,5-bis-phosphate carboxylase (ssRUBISCO) (Coruzzi et al., EMBO J. 3:1671–1679 (1984), the rice cytosolic triosephosphate isomerase (TPI) promoter (Xu et al. Plant Physiol. 106:459–467 (1994), the adenine phosphoribosyltransferase (APRT) promoter of Arabidopsis (Moffatt et al. Gene 143:211–216 (1994), the rice actin 1 gene promoter (Zhong et al. Plant Sci. 116:73–84 (1996), the mannopine synthase and octopine synthase promoters (Ni et al. Plant J. 7:661–676 (1995), the Adh promoter (Walker et al., Proc. Natl. Acad. Sci. U.S.A. 84: 6624–6628 (1987), the sucrose synthase promoter (Yang et al., Proc. Natl. Acad. Sci. U.S.A. 87: 4144–4148 (1990), the R gene complex promoter (Chandler et al., The Plant Cell 1:1175–1183 (1989), and the chlorophyll α/β binding protein gene promoter, et cetera These promoters have been used to create DNA vectors that have been expressed in plants; see, e.g., PCT publication WO 8402913. All of these promoters have been used to create various types of plant-expressible recombinant DNA vectors. Comparative analysis of constitutive promoters by the expression of reporter genes such as the uidA (β-glucuronidase) gene from *E. coli* has been performed with many of these and other promoters (Li et al. Mol. Breeding 3:1–14 (1997); Wen et al. Chinese J. of Bot. 5:102–109 (1993). Promoters that are known or are found to cause transcription of DNA in plant cells can be used in the present invention. Such promoters may be obtained from a variety of sources such as plants and plant viruses. In addition to promoters that are known to cause transcription of DNA in plant cells, other promoters may be identified for use in the current invention by screening a plant cDNA library for genes that are selectively or preferably expressed in the target tissues or cells. For the purpose of expression in source tissues of the plant, such as the leaf, seed, root or stem, it is preferred that the promoters utilized in the present invention have relatively high expression in these specific tissues. For this purpose, one may choose from a number of promoters for genes with tissue- or cell-specific or -enhanced expression. Examples of such promoters reported in the literature include the chloroplast glutamine synthetase GS2 promoter from pea (Edwards et al., Proc. Natl. Acad. Sci. U.S.A. 87: 3459–3463 (1990), the chloroplast fructose-1,6-biphosphatase (FBPase) promoter from wheat (Lloyd et al., Mol. Gen. Genet. 225: 209–216 (1991), the nuclear photosynthetic ST-LS1 promoter from potato (Stockhaus et al., EMBO J. 8: 2445–2451, (1989), the serine/threonine kinase (PAL) promoter and the glucoamylase (CHS) promoter from *Arabidopsis thaliana*. Also reported to be active in photosynthetically active tissues are the ribulose-1,5-bisphosphate carboxylase (RBCS) promoter from eastern larch (*Larix laricina*), the promoter for the Cab gene, Cab6, from pine (Yamamoto et al., Plant Cell Physiol. 35: 773–778 (1994), the promoter for the Cab-1 gene from wheat (Fejes et al., Plant Mol. Biol. 15: 921–932 (1990), the promoter for the Cab-1 gene from spinach (Lubberstedt et al., Plant Physiol. 104:997–1006 (1994), the promoter for the Cab1R gene from rice (Luan et al., Plant Cell. 4:971–981 (1992), the pyruvate, orthophosphate dikinase (PPDK) promoter from *Zea mays* (Matsuoka et al., Proc. Natl. Acad. Sci. U.S.A. 90: 9586–9590 (1993), the promoter for the tobacco Lhcb1*2 gene (Cerdan et al., Plant Mol. Biol. 33:245–255 (1997), the *Arabidopsis thaliana* Suc2 sucrose-H$^+$ symporter promoter (Truernit et al., Planta. 196:564–570 (1995), and the promoter for the thylakoid membrane protein genes from spinach (PsaD, PsaF, PsaE, PC, FNR, AtpC, AtpD, Cab, RbcS).

Other promoters for the chlorophyll α/β-binding proteins may also be utilized in the present invention, such as the promoters for LhcB gene and PsbP gene from white mustard (*Sinapis alba*) (Kretsch et al., Plant Mol. Biol. 28: 219–229 (1995). A variety of plant gene promoters that are regulated in response to environmental, hormonal, chemical, and/or developmental signals, also can be used for expression of RNA-binding protein genes in plant cells, including promoters regulated by (1) heat (Callis et al., Plant Physiol. 88:965–968 (1988), (2) light (e.g., pea RbcS-3A promoter, Kuhlemeier et al., Plant Cell 1:471–478 (1989); maize RbcS promoter, Schaffner et al., Plant Cell 3:997–1012 (1991); (3) hormones, such as abscisic acid (Marcotte et al., Plant Cell 1:969–976 (1989), (4) wounding (e.g., Wuni, Siebertz et al., Plant Cell 1:961–968 (1989); or (5) chemicals, such as methyl jasminate, salicylic acid, steroid hormones, alcohol, Safeners (Gatz, Curr. Opin. Biotech 7:168–172 (1996), WO 9706269), or it may also be advantageous to employ (6) organ-specific promoters (e.g., Roshal et al., EMBO J. 6:1155- (1987); Schernthaner et al., EMBO J. 7:1249–1255 (1988); Bustos et al., Plant Cell 1:839–853 (1989).

For the purpose of expression in sink tissues of the plant, such as the tuber of the potato plant, the fruit of tomato, or the seed of soybean, canola, cotton, *Zea mays*, wheat, rice, and barley, it is preferred that the promoters utilized in the present invention have relatively high expression in these specific tissues. A number of promoters for genes with tuber-specific or -enhanced expression are known, including the class I patatin promoter (Bevan et al., EMBO J. 8:1899–1906 (1986); Jefferson et al., Plant Mol. Biol. 14:995–1006 (1990), the promoter for the potato tuber ADPGPP genes, both the large and small subunits, the sucrose synthase promoter (Salanoubat et al., Gene 60:47–56 (1987); Salanoubat et al., Gene 84:181–185 (1989), the promoter for the major tuber proteins including the 22 kD protein complexes and proteinase inhibitors (Hannapel, Plant Physiol. 101:703–704 (1993), the promoter for the granule bound starch synthase gene (GBSS) (Visser et al., Plant Mol. Biol. 17:691–699 (1991), and other class I and II patatins promoters (Koster-Topfer et al., Mol. Gen. Genet. 219:390–396 (1989); Mignery et al., Gene 62:27–44 (1988). Other promoters can also be used to express a protein in specific tissues, such as seeds or fruits. The promoter for β-conglycinin (Chen et al., Dev. Genet. 10:112–122 (1989) or other seed-specific promoters such as the napin and phaseolin promoters, can be used. The zeins are a group of storage proteins found in *Zea mays* endosperm. Genomic clones for zein genes have been isolated (Pedersen et al., Cell 29:1015–1026 (1982), and the promoters from these clones, including the 15 kd1), 16 kD, 19 kD, 22 kD, 27 kD, and gamma genes, could also be used. Other promoters known to function, for example, in *Zea mays* include the promoters for the following genes: waxy, Brittle, Shrunken 2, Branching enzymes I and II, starch synthases, debranching enzymes, oleosins, glutelins, and sucrose synthases. A particularly preferred promoter for *Zea mays* endosperm expression is the promoter for the glutelin gene from rice, more particularly the Osgt-1 promoter (Zheng et al., Mol. Cell Biol. 13:5829–5842 (1993). Examples of promoters suitable for expression in wheat include those promoters for the ADPglucose pyrosynthase (ADPGPP) subunits, the granule bound and other starch synthase, the branching and debranching enzymes, the embryogenesis-abundant proteins, the gliadins, and the glutenins. Examples of such promoters in rice include those promoters for the ADPGPP subunits, the granule bound and other starch synthase, the branching enzymes, the debranching enzymes, sucrose synthases, and the glutelins. A particularly preferred promoter is the promoter for rice glutelin, Osgt-1 gene. Examples of such promoters for barley include those for the ADPGPP subunits, the granule bound and other starch synthase, the branching enzymes, the debranching enzymes, sucrose synthases, the hordeins, the embryo globulins, and the aleurone specific proteins.

Root specific promoters may also be used. An example of such a promoter is the promoter for the acid chitinase gene (Samac et al., Plant Mol. Biol. 25:587–596 (1994). Expression in root tissue could also be accomplished by utilizing the root specific subdomains of the CaMV 35S promoter that have been identified (Lam et al., Proc. Natl. Acad. Sci. U.S.A. 86: 7890–7894 (1989). Other root cell specific promoters include those reported by Conkling et al. (Plant Physiol. 93: 1203–1211 (1990).

The 5' non-translated leader sequence can be derived from the promoter selected to express the heterologous gene sequence of the DNA molecule of the present invention, and can be specifically modified if desired so as to increase translation of mRNA. For a review of optimizing expression of transgenes, see Koziel et al., (Plant Mol. Biol. 32:393–405 (1996). The 5' non-translated regions can also be obtained from plant viral RNAs (Tobacco mosaic virus, Tobacco etch virus, Maize dwarf mosaic virus, Alfalfa mosaic virus, among others) from suitable eukaryotic genes, plant genes (wheat and maize chlorophyll a/b binding protein gene leader), or from a synthetic gene sequence. The present invention is not limited to constructs wherein the non-translated region is derived from the 5' non-translated sequence that accompanies the promoter sequence. The leader sequence could also be derived from an unrelated promoter or coding sequence. Leader sequences useful in context of the present invention comprise the maize Hsp70 leader (U.S. Pat. No. 5,362,865 and U.S. Pat. No. 5,859,347), and the TMV omega element (Gallie et al., The Plant Cell 1:301–311 (1989).

A vector or construct may also include various regulatory elements. Intron sequences are known in the art to aid in the expression of transgenes in monocot plant cells. Examples of such introns include the Adh intron 1 (Callis et al., Genes and Develop. 1:1183–1200 (1987), the sucrose synthase intron (Vasil et al., Plant Physiol. 91:1575–1579 (1989), U.S. Pat. No. 5,955,330), first intron of the rice actin gene (U.S. Pat. No. 5,641,876).

A vector may also include a transit peptide nucleic acid sequence. The glyphosate target in plants, the 5-enolpyruvyl-shikimate-3-phosate synthase (EPSPS) enzyme, is located in the chloroplast. Many chloroplast-localized proteins, including EPSPS, are expressed from nuclear genes as precursors and are targeted to the chloroplast by a chloroplast transit peptide (CTP) that is removed during the import steps. Examples of other such chloroplast proteins include the small subunit (SSU) of Ribulose-1,5-bisphosphate carboxylase, Ferredoxin, Ferredoxin oxidoreductase, the light-harvesting complex protein I and protein II, and Thioredoxin F. It has been demonstrated in vivo and in vitro that non-chloroplast proteins may be targeted to the chloroplast by use of protein fusions with a CTP and that a CTP sequence is sufficient to target a protein to the chloroplast. Incorporation of a suitable chloroplast transit peptide, such as, the *Arabidopsis thaliana* EPSPS CTP (Klee et al., Mol. Gen. Genet. 210:437–442 (1987), and the *Petunia hybrida* EPSPS CTP (della-Cioppa et al., Proc. Natl. Acad. Sci. USA 83:6873–6877 (1986) has been show to target heterologous EPSPS protein sequences to chloroplasts in transgenic plants. The production of glyphosate tolerant plants by expression of a fusion protein comprising an amino-terminal CTP with a glyphosate resistant EPSPS enzyme is well known by those skilled in the art, (U.S. Pat. No. 5,627,061, U.S. Pat. No. 5,633,435, U.S. Pat. No. 5,312,910, EP 0218571, EP 189707, EP 508909, and EP 924299). Those skilled in the art will recognize that various chimeric constructs can be made that utilize the functionality of a particular CTP to import glyphosate resistant EPSPS enzymes into the plant cell chloroplast.

The termination of transcription is accomplished by a 3' non-translated DNA sequence operably linked in the chimeric vector to the gene of interest. The 3' non-translated region of a recombinant DNA molecule contains a polyadenylation signal that functions in plants to cause the addition of adenylate nucleotides to the 3' end of the RNA. The 3' non-translated region can be obtained from various genes that are expressed in plant cells. The nopaline synthase 3' untranslated region (Fraley et al., Proc. Natl. Acad. Sci. 80:4803–4807 (1983), the 3' untranslated region from pea small subunit Rubisco gene (Coruzzi et al., EMBO J. 3:1671–1679 (1994), the 3' untranslated region from soybean 7S seed storage protein gene (Schuler et al., Nuc Acids Res. 10:8225–8244 (1982) are commonly used in this capacity. The 3' transcribed, non-translated regions containing the polyadenylate signal of Agrobacterium tumor-inducing (Ti) plasmid genes are also suitable.

The aforesaid described genetic elements and other regulatory elements of similar function may be substituted when appropriate by those skilled in the art of plant molecular biology to provide necessary function to the plant expression cassette. DNA constructs for glyphosate tolerance designed for expression in plastids will necessarily contain genetic elements that function in plastids.

A vector may also include a screenable or scorable marker gene. Screenable or scorable markers may be used to monitor expression. Exemplary markers include a β-glucuronidase or uidA gene (GUS) that encodes an enzyme for that various chromogenic substrates are known (Jefferson, Plant Mol. Biol, Rep. 5:387–405 (1987); Jefferson et al., EMBO J. 6:3901–3907 (1987); an R-locus gene, that encodes a product that regulates the production of anthocyanin pigments (red color) in plant tissues (Dellaporta et al., Stadler Symposium 11:263–282 (1988); a β-lactamase gene (Sutcliffe et al., Proc. Natl. Acad. Sci. (U.S.A.) 75:3737–3741 (1978); a gene that encodes an enzyme for that various chromogenic substrates are known (e.g., PADAC, a chromogenic cephalosporin); a luciferase gene (Ow et al., Science 234:856–859 (1986); a xylE gene (Zukowsky et al., Proc. Natl. Acad. Sci. (U.S.A.) 80:1101–1105 (1983) that encodes a catechol dioxygenase that can convert chromogenic catechols; an α-amylase gene (Ikatu et al., *Bio/Technol.* 8:241–242 (1990); a tyrosinase gene (Katz et al., J. Gen. Microbiol. 129:2703–2714 (1983) that encodes an enzyme capable of oxidizing tyrosine to DOPA and dopaquinone that in turn condenses to melanin; green flourescence protein (Elliot et al., Plant cell Rep. 18:707–714 (1999) and an α-galactosidase.

Included within the terms "selectable or screenable marker genes" are also genes that encode a secretable marker whose secretion can be detected as a means of identifying or selecting for transformed cells. Examples include markers that encode a secretable antigen that can be identified by antibody interaction, or even secretable enzymes that can be detected catalytically. Secretable proteins fall into a number of classes, including small, diffusible proteins that are detectable, (e.g., by ELISA), small active enzymes that are detectable in extracellular solution (e.g., α-amylase, β-lactamase, phosphinothricin transferase), or proteins that are inserted or trapped in the cell wall (such as proteins that include a leader sequence such as that found in the expression unit of extension or tobacco PR-S). Other possible selectable and/or screenable marker genes will be apparent to those of skill in the art.

There are many methods for introducing transforming nucleic acid molecules into plant cells. Suitable methods are believed to include virtually any method shown effective in introducing the nucleic acid molecules into a plant cell, such as by Agrobacterium infection or direct delivery of nucleic acid molecules.

Four general methods for direct delivery of a gene into cells have been described: (1) chemical methods (Graham et al., Virology 54:536–539 (1973); (2) physical methods such as microinjection (Capecchi, Cell 22:479–488 (1980); electroporation (Wong et al., Biochem. Biophys. Res. Commun. 107:584–587 (1982); Fromm et al., Proc. Natl. Acad. Sci. (U.S.A.) 82:5824–5828 (1985); (U.S. Pat. No. 5,384,253); and the gene gun (Johnston et al., Methods Cell Biol.

43:353–365 (1994); (3) viral vectors (Clapp, Clin. Perinatol. 20:155–168 (1993); Lu et al., J. Exp. Med. 178:2089–2096 (1993); Eglitis et al., Biotechniques 6:608–614 (1988); and (4) receptor-mediated mechanisms (Curiel et al., Hum. Gen. Ther. 3:147–154 (1992), Wagner et al., Proc. Natl. Acad. Sci. USA 89:6099–6103 (1992).

Acceleration methods that may be used include, for example, microprojectile bombardment and the like. One example of a method for delivering transforming nucleic acid molecules to plant cells is microprojectile bombardment. This method has been reviewed by Yang et al., Particle Bombardment Technology for Gene Transfer, Oxford Press, Oxford, England (1994). Non-biological particles (microprojectiles) that may be coated with nucleic acids and delivered into cells by a propelling force. Exemplary particles include those comprised of tungsten, gold, platinum, and the like. A particular advantage of microprojectile bombardment, in addition to it being an effective means of reproducibly transforming monocots, is that neither the isolation of protoplasts (Cristou et al., Plant Physiol. 87:671–674 (1988), nor the susceptibility of Agrobacterium infection are required. An illustrative embodiment of a method for delivering DNA into Zea mays cells by acceleration is a biolistics α-particle delivery system, that can be used to propel particles coated with DNA through a screen, such as a stainless steel or Nytex screen, onto a filter surface covered with corn cells cultured in suspension. Gordon-Kamm et al., describes the basic procedure for coating tungsten particles with DNA (Gordon-Kamm et al., Plant Cell 2:603–618 (1990). The screen disperses the tungsten nucleic acid particles so that they are not delivered to the recipient cells in large aggregates. A particle delivery system suitable for use with the present invention is the helium acceleration PDS-1000/He gun is available from Bio-Rad Laboratories (Bio-Rad, Hercules, Calif.) (Sanford et al., Technique 3:3–16 (1991).

For the bombardment, cells in suspension may be concentrated on filters. Filters containing the cells to be bombarded are positioned at an appropriate distance below the microprojectile stopping plate. If desired, one or more screens are also positioned between the gun and the cells to be bombarded.

Alternatively, immature embryos or other target cells may be arranged on solid culture medium. The cells to be bombarded are positioned at an appropriate distance below the microprojectile stopping plate. If desired, one or more screens are also positioned between the acceleration device and the cells to be bombarded. Through the use of techniques set forth herein one may obtain up to 1000 or more foci of cells transiently expressing a marker gene. The number of cells in a focus that express the exogenous gene product 48 hours post-bombardment often range from one to ten and average one to three.

In bombardment transformation, one may optimize the pre-bombardment culturing conditions and the bombardment parameters to yield the maximum numbers of stable transformants. Both the physical and biological parameters for bombardment are important in this technology. Physical factors are those that involve manipulating the DNA/microprojectile precipitate or those that affect the flight and velocity of either the macro- or microprojectiles. Biological factors include all steps involved in manipulation of cells before and immediately after bombardment, the osmotic adjustment of target cells to help alleviate the trauma associated with bombardment, and also the nature of the transforming DNA, such as linearized DNA or intact supercoiled plasmids. It is believed that pre-bombardment manipulations are especially important for successful transformation of immature embryos.

In another alternative embodiment, plastids can be stably transformed. Method disclosed for plastid transformation in higher plants include particle gun delivery of DNA containing a selectable marker and targeting of the DNA to the plastid genome through homologous recombination (Svab et al. Proc. Natl. Acad. Sci. (U.S.A.) 87:8526–8530 (1990); Svab et al., Proc. Natl. Acad. Sci. (U.S.A.) 90:913–917 (1993); (Staub et al., EMBO J. 12:601–606 (1993). The methods disclosed in U.S. Pat. No. 5,451,513, U.S. Pat. No. 5,545,818, U.S. Pat. No. 5,877,402, U.S. Pat. No. 5,932479, and WO 99/05265.

Accordingly, it is contemplated that one may wish to adjust various aspects of the bombardment parameters in small scale studies to fully optimize the conditions. One may particularly wish to adjust physical parameters such as gap distance, flight distance, tissue distance, and helium pressure. One may also minimize the trauma reduction factors by modifying conditions that influence the physiological state of the recipient cells and that may therefore influence transformation and integration efficiencies. For example, the osmotic state, tissue hydration and the subculture stage or cell cycle of the recipient cells may be adjusted for optimum transformation. The execution of other routine adjustments will be known to those of skill in the art in light of the present disclosure.

Agrobacterium-mediated transfer is a widely applicable system for introducing genes into plant cells because the DNA can be introduced into whole plant tissues, thereby bypassing the need for regeneration of an intact plant from a protoplast. The use of Agrobacterium-mediated plant integrating vectors to introduce DNA into plant cells is well known in the art. See, for example the methods described by Fraley et al., Bio/Technology 3:629–635 (1985) and Rogers et al., Methods Enzymol. 153:253–277 (1987). Further, the integration of the T-DNA is a relatively precise process resulting in few rearrangements. The region of DNA to be transferred is defined by the border sequences, and intervening DNA is usually inserted into the plant genome as described (Spielmann et al., Mol. Gen. Genet. 205:34 (1986).

Modern Agrobacterium transformation vectors are capable of replication in E. coli as well as Agrobacterium, allowing for convenient manipulations as described (Klee et al., In: Plant DNA Infectious Agents, Hohn and Schell, eds., Springer-Verlag, New York, pp. 179–203 (1985). Moreover, technological advances in vectors for Agrobacterium-mediated gene transfer have improved the arrangement of genes and restriction sites in the vectors to facilitate construction of vectors capable of expressing various polypeptide coding genes. The vectors described have convenient multi-linker regions flanked by a promoter and a polyadenylation site for direct expression of inserted polypeptide coding genes and are suitable for present purposes (Rogers et al., Methods Enzymol. 153:253–277 (1987). In addition, Agrobacterium containing both armed and disarmed Ti genes can be used for the transformations. In those plant varieties where Agrobacterium-mediated transformation is efficient, it is the method of choice because of the facile and defined nature of the gene transfer.

A transgenic plant formed using Agrobacterium transformation methods typically contains a single genetic locus on one chromosome. Such transgenic plants can be referred to as being hemizygous for the added gene. More preferred is a transgenic plant that is homozygous for the added structural gene; i.e., a transgenic plant that contains two added genes, one gene at the same locus on each chromosome of a chromosome pair. A homozygous transgenic plant can be obtained by sexually mating (selfing) an independent segregant transgenic plant that contains a single added gene, germinating some of the seed produced and analyzing the resulting plants for the gene of interest.

It is also to be understood that two different transgenic plants can also be mated to produce offspring that contain two independently segregating exogenous genes. Selfing of appropriate progeny can produce plants that are homozygous for both exogenous genes. Back-crossing to a parental plant and out-crossing with a non-transgenic plant are also contemplated, as is vegetative propagation. Descriptions of other breeding methods that are commonly used for different traits and crops can be found in Fehr, In: *Breeding Methods for Cultivar Development*, Wilcox J. ed., American Society of Agronomy, Madison Wis. (1987).

Transformation of plant protoplasts can be achieved using methods based on calcium phosphate precipitation, polyethylene glycol treatment, electroporation, and combinations of these treatments (see, e.g., Potrykus et al., Mol. Gen. Genet. 205:193–200 (1986); Lorz et al., Mol. Gen. Genet. 199:178 (1985); Fromm et al., Nature 319:791 (1986); Uchimiya et al., Mol. Gen. Genet. 204:204 (1986); Marcotte et al., Nature 335:454–457 (1988). Application of these systems to different plant varieties depends upon the ability to regenerate that particular plant strain from protoplasts. Illustrative methods for the regeneration of cereals from protoplasts are described (Fujimura et al., Plant Tissue Culture Letters 2:74 (1985); Toriyama et al., Theor Appl. Genet. 205:34 (1986); Yamada et al., Plant Cell Rep. 4:85 (1986); Abdullah et al., Biotechnology 4:1087 (1986).

Other methods of cell transformation can also be used and include but are not limited to introduction of DNA into plants by direct DNA transfer into pollen (Hess et al., Intern Rev. Cytol. 107:367 (1987); Luo et al., Plant Mol Biol. Reporter 6:165 (1988), by direct injection of DNA into reproductive organs of a plant (Pena et al., Nature 325:274 (1987), or by direct injection of DNA into the cells of immature embryos followed by the rehydration of desiccated embryos (Neuhaus et al., Theor. Appl. Genet. 75:30 (1987).

The regeneration, development, and cultivation of plants from single plant protoplast transformants or from various transformed explants is well known in the art (Weissbach et al., In: *Methods for Plant Molecular Biology*, Academic Press, San Diego, Calif., (1988). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous gene is well known in the art. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired exogenous nucleic acid is cultivated using methods well known to one skilled in the art.

Methods for transforming dicots, primarily by use of *Agrobacterium tumefaciens*, and obtaining transgenic plants have been published for cotton (U.S. Pat. No. 5,004,863, U.S. Pat. No. 5,159,135, U.S. Pat. No. 5,518,908); soybean (U.S. Pat. No. 5,569,834, U.S. Pat. No. 5,416,011, McCabe et. al., Bio/Technology 6:923 (1988), Christou et al., Plant Physiol. 87:671–674 (1988); Brassica (U.S. Pat. No. 5,463, 174); peanut (Cheng et al., Plant Cell Rep. 15:653–657 (1996), McKently et al., Plant Cell Rep. 14:699–703 (1995); and pea (Grant et al., Plant Cell Rep. 15:254–258, (1995).

Transformation of monocotyledons using electroporation, particle bombardment, and Agrobacterium have also been reported. Transformation and plant regeneration have been achieved in asparagus (Bytebier et al., Proc. Natl. Acad. Sci. (USA) 84:5354–5349 (1987); barley (Wan et al., Plant Physiol 104:37–48 (1994); *Zea mays* (Rhodes et al., Science 240:204–207 (1988), Gordon-Kamm et al., Plant Cell 2:603–618 (1990), Fromm et al., Bio/Technology 8:833–839 (1990), Koziel et al., Bio/Technology 11:194–200 (1993), Armstrong et al., Crop Science 35:550–557 (1995); oat (Somers et al., Bio/Technology 10:1589–1594 (1992); orchard grass (Horn et al., Plant Cell Rep. 7:469–472 (1988); rice (Toriyama et al., Theor Appl. Genet. 205:34-(1986), Part et al., Plant Mol. Biol. 32:1135–1148, (1996), Abedinia et al., Aust. J. Plant Physiol. 24:133–141 (1997), Battraw et al., Plant Mol. Biol. 15:527–538 (1990), Christou et al., Bio/Technology 9:957–962 (1991); rye (De la Pena et al., Nature 325:274–276 (1987); sugarcane (Bower et al., Plant J. 2:409–416 (1992); tall fescue (Wang et al., Bio/Technology 10:691–696 (1992); and wheat (Vasil et al., Bio/Technology 10:667–674 (1992); U.S. Pat. No. 5,631, 152).

Assays for gene expression based on the transient expression of cloned nucleic acid vectors have been developed by introducing the nucleic acid molecules into plant cells by polyethylene glycol treatment, electroporation, or particle bombardment (Marcotte et al., Nature 335:454–457 (1988); Marcotte et al., Plant Cell 1:523–532 (1989); McCarty et al., Cell 66:895–905 (1991); Hattori et al., Genes Dev. 6:609–618 (1992); Goff et al., EMBO J. 9:2517–2522 (1990). Transient expression systems may be used to functionally dissect gene constructs (see generally, Mailga et al., Methods in Plant Molecular Biology, Cold Spring Harbor Press (1995). It is understood that any of the nucleic acid molecules of the present invention can be introduced into a plant cell in a permanent or transient manner in combination with other genetic elements such as promoters, leaders, transit peptide sequences, enhancers, introns, 3' nontranslated regions and other elements known to those skilled in the art that are useful for control of transgene expression in plants.

*Eleusine indica* has been shown to hybridize with *Eleusine coracana* (finger millet), an important cultivated millet of India and East Africa (Chennaveeraiah et al., Euphytica 2–3:489–495, (1974). Classical plant breeding methods can be used to transfer the gene and the glyphosate tolerant phenotype to crop plants within the family Poaceae. The DNA molecules of the EPSPS glyphosate resistance gene of *E. indica* (SEQ ID NO:6) can be used as a probe to identify other like DNA molecules by standard methods. Oligonucleotide DNA molecules homologous or complementary to the EPSPS glyphosate resistance gene of *E. indica* can be used in a marker assisted breeding method (Simple sequence repeat DNA marker analysis, in "DNA markers: Protocols, applications, and overviews: (1997) 173–185, Cregan, et al., eds., Wiley-Liss NY) to assist in the breeding of this gene into related and heterologous crop species.

In addition to the above discussed procedures, practitioners are familiar with the standard resource materials that describe specific conditions and procedures for the construction, manipulation and isolation of macromolecules (e.g., DNA molecules, plasmids, etc.), generation of recombinant organisms and the screening and isolating of clones, (see for example, Sambrook et al., Molecular Cloning: A Laboratory Manual, Cold Spring Harbor Press (1989); Mailga et al., Methods in Plant Molecular Biology, Cold Spring Harbor Press (1995); Birren et al., Genome Analysis: Detecting Genes, 1, Cold Spring Harbor, N.Y. (1998); Birren et al., Genome Analysis: Analyzing DNA, 2, Cold Spring Harbor, N.Y. (1998); Clark et al., Plant Molecular Biology: A Laboratory Manual, Springer, N.Y. (1997); and Innis et al., PCR Protocols: A Guide to Methods and Applications, Academic Press: San Diego, (1990).

Plant species containing a naturally occurring EPSPS enzyme resistant to glyphosate have not been previously reported. The subject of this invention is the EPSPS enzyme isolated from *Eleusine indica* that has been shown to be resistant to glyphosate and the expression of the DNA molecule encoding this EPSPS enzyme in other plants that then confers glyphosate tolerance to those recipient plants. The glyphosate resistant EPSPS enzyme isolated from *Eleusine indica* glyphosate tolerant biotype has a novel $K_m$ with respect to binding of PEP as compared to other plant EPSP Synthases that have been modified for glyphosate resistance by a single amino acid substitution of a proline to serine substitution in the active site of the enzyme. The $K_m$ for PEP of the *E. indica* glyphosate resistant enzyme is little changed from the *E. indica* glyphosate sensitive EPSPS enzyme. In addition, this gene is from a monocot plant and hence may not need nucleic sequence modification to affect expression in transgenic monocot crop plants. The *E. indica* glyphosate tolerant EPSPS enzyme amino acid sequence can be modified by site directed mutation to include other known substitutions.

The present invention also provides for parts of the plants of the present invention. Plant parts, without limitation, include seed, endosperm, ovule and pollen. In a particularly preferred embodiment of the present invention, the plant part is a seed.

The following examples are included to demonstrate examples of certain preferred embodiments of the invention. It should be appreciated by those of skill in the art that the techniques disclosed in the examples that follow represent approaches the inventors have found function well in the practice of the invention, and thus can be considered to constitute examples of preferred modes for its practice. However, those of skill in the art should, in light of the present disclosure, appreciate that many changes can be made in the specific embodiments that are disclosed and still obtain a like or similar result without departing from the spirit and scope of the invention. All references cited herein are hereby expressly incorporated herein by reference.

Seeds from glyphosate tolerant *Eleusine indica* plants were deposited with the American Type Culture Collection (ATCC, 10801 University Blvd, Manassas, Va., U.S.A., 20110–2209) and assigned ATCC No. PTA-2177. The deposit will be maintained in the depository for a period of 30 years, or 5 years after the last request, or for the effective life of the patent, whichever is longer, and will be replaced as necessary during that period.

EXAMPLE 1

*Eleusine indica* plants tolerant to glyphosate were collected from a site near Johor, Malaysia. Glyphosate tolerant biotypes of *E. indica* are identified and numbered. Seed is collected from each biotype and planted in pots in the greenhouse. Clones are generated for each plant by excising 10–20 tillers and transplanting these in separate pots. Glyphosate sensitive and tolerant individual plants are then identified by treatment with glyphosate at either 0.5 kg active ingredient (ai)/hectare (ha) or 2.0 kg ai/ha, respectively. A corresponding clone for glyphosate tolerant and glyphosate sensitive *E. indica* biotype is left untreated. These clones are used as the source of fresh tissue for enzyme analysis and gene isolation.

Construction of a cDNA library from the glyphosate tolerant *E. indica* biotype and the glyphosate sensitive *E. indica* biotype is performed by isolating total RNA from the crown tissues. The crown tissues are dissected from the plants, then flash-frozen with liquid nitrogen and maintained at −80° C. until needed. Total RNAs are extracted from frozen crown samples using the RNeasy Plant Mini Kit (cat.#74904, Qiagen Inc., Valencia, Calif.) per manufacturer's instructions. Oligo dT-primed first-strand cDNAs are prepared from 5 μg samples of total RNA using the Superscript Pre-Amplification System (cat.#18089-011, Life Technologies, Rockville, Md.) per manufacturer's instructions. Two μl of first-strand cDNA are then used to generate partial *E. indica* EPSP synthase cDNAs via polymerase chain reaction using a modification of the "touchdown PCR" technique (Don et al., Nucl. Acids Res. 19:4008, 1991). Degenerate oligonucleotide pools of SEQ ID NO:1 and SEQ ID NO:2 are added in a 50 μl RT-PCR reaction at a final concentration of 25 μM.

| | |
|---|---|
| 5'-TNWSNGTNGARGCNGAYAARGT-3' | (SEQ ID NO:1) |
| 5'-GCCATNGCCATNCKRTGRTCRTC-3' | (SEQ ID NO:2) |

PCR amplifications are then performed using the Expand High Fidelity PCR System (cat.#1 732 641, Roche Molecular Biochemicals, Indianapolis, Ind.) per manufacturer's instructions. A thermal profile of 94° C. for 20 seconds, followed by 60° C. for 1 minute, then 72° C. for 1 minute 30 seconds is used for the initial 30 cycles with a 0.5° C. decrease in annealing temperature per cycle. This is followed by 10 additional cycles of 94° C. for 20 seconds, 45° C. for 1 minute, then 72° C. for 1 minute 30 seconds.

RT-PCR products are then purified by agarose gel electrophoresis using a QIAquick Gel Extraction Kit (cat.#28704, Qiagen Inc., Valencia, Calif.) then directly cloned into the pCR2.1-TOPO vector (cat.#K4500-40, Invitrogen, Carlsbad, Calif.). The identity of the cloned RT-PCR products is confirmed by DNA sequence analysis (ABI Prism™ 377, Perkin Elmer, Foster City, Calif.).

The remainder of the 3' end of the EPSP synthase coding region is generated using the 3' RACE System for Rapid Amplification of cDNA Ends (cat.#18373-027, Life Technologies, Rockville, Md.), using the gene-specific oligonucleotide of SEQ ID NO:3. The cDNA is prepared according to manufacturer's instructions using 5 μg of total RNA isolated from crown tissues as previously described. 5'-GTGAAAGCAGAGCATTCTGATAGC-3' (SEQ ID NO: 3)

PCR amplifications are conducted in 50 μl reactions including 5 μl first-strand cDNA reaction, 20 picomoles of each primer, 10 mM TrisHCl (pH 8.3), 50 mM KCl, 1.5 mM $MgCl_2$, 200 μM dNTPs, and 2.5 units Taq polymerase. A thermal profile of 94° C. for 20 seconds, followed by 57° C. for 1 minute, then 72° C. for 1 minute 30 seconds is used for 35 cycles. The identity of the 3'-RACE products is confirmed by DNA sequence analysis (ABI Prism™ 377, Perkin Elmer, Foster, Calif.).

The remainder of the 5' end of the *E. indica* EPSP synthase mature protein coding region is generated using the SMART RACE cDNA Amplification Kit (cat.#K1811-1, Clontech Laboratories Inc., Palo Alto, Calif.), using the gene-specific oligonucleotides of SEQ ID NO:4 and SEQ ID NO:5. The cDNA is prepared according to manufacturer's instructions using 150 ng of polyA+ mRNA isolated from crown tissues using an Oligotex mRNA Midi Kit (cat.#28704, Qiagen Inc., Valencia, Calif.).

5'-GGCTGCTGTCAATGTCGCATTGCAGTTCC-3'  (SEQ ID NO:4)

5'-CTCTTTCGCATCCTTCTCAACTGGGAACTTGC-3'  (SEQ ID NO:5)

PCR reactions are conducted as recommended by the manufacturer, except that the Expand High Fidelity PCR System (cat.#1 732 641, Roche Molecular Biochemicals, Indianapolis, Ind.) is used and DMSO is included in all reactions at a final concentration of 5.0% to facilitate the amplification of GC-rich sequences. The synthetic DNA oligonucleotide described in SEQ ID NO:4 is used in the primary amplifications, then second round ("nested") amplifications are performed using the oligonucleotide described in SEQ ID NO: 5, with a 1 μl aliquot of 1:100 dilution of the primary PCR reactions. The identity of the 5'-RACE products is confirmed by DNA sequence analysis (ABI Prisms™ 377, Perkin Elmer, Foster City, Calif.).

Figure 1:
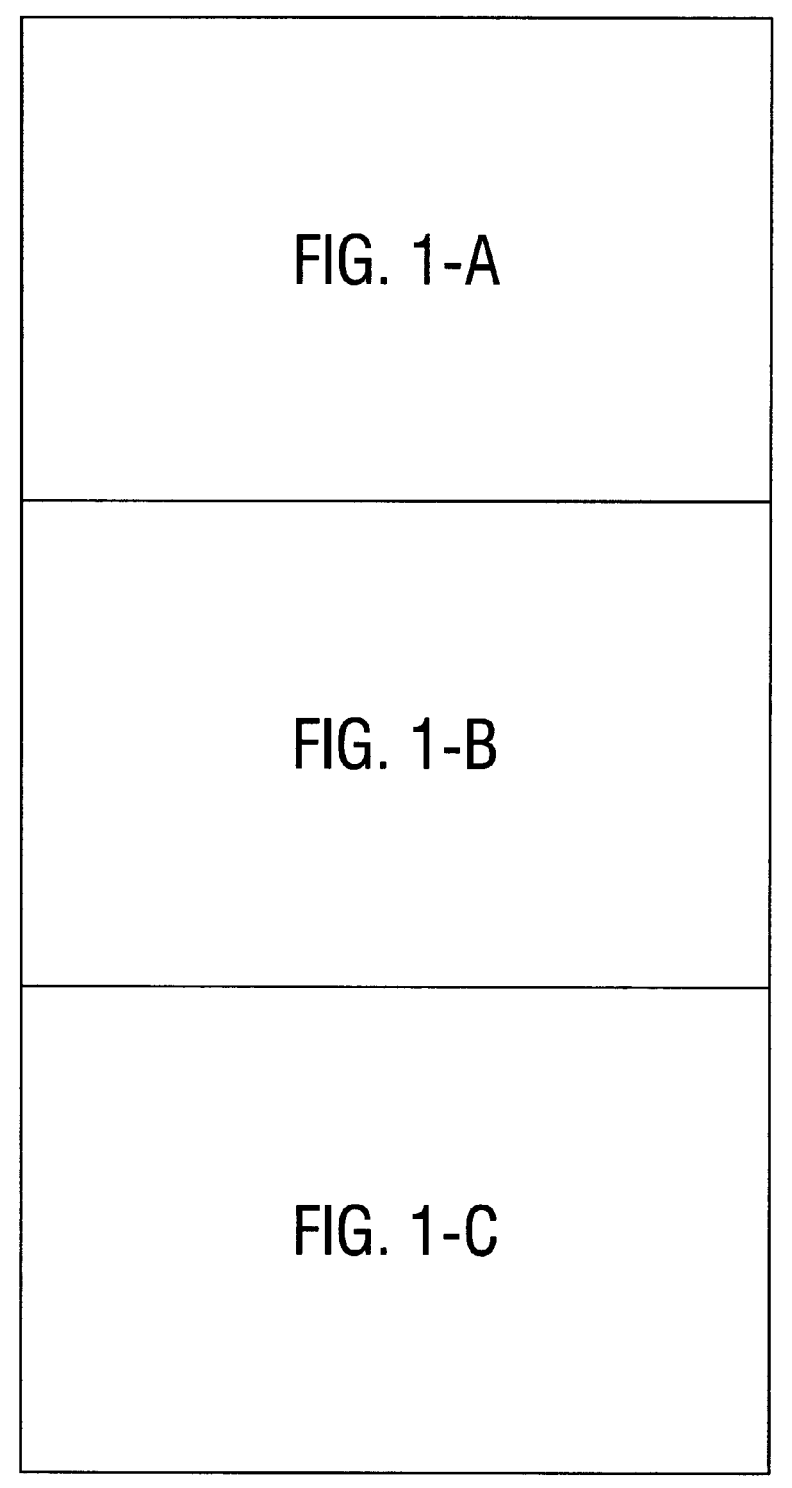

The significant overlap of sequences generated by RT-PCR, 3' RACE, and 5' RACE allows for the unambiguous assembly of the sequences into a single DNA sequence containing the entire open reading frame for the mature protein, using the SEQMan II software package (DNASTAR Inc., Madison, Wis.). The DNA sequence corresponding to the mature protein-coding region of the *Eleusine indica* (glyphosate tolerant biotype) EPSP synthase gene (SEQ ID NO:6) is shown in FIG. 1.

The deduced amino acid sequence for the mature protein-coding region of the *Eleusine indica* (glyphosate tolerant biotype) EPSP synthase gene (SEQ ID NO:7) for this protein is shown in FIG. 2.

EXAMPLE 2

EPSP synthase enzyme from the glyphosate tolerant *E. indica* biotype confers increased glyphosate tolerance in transgenic *E. coli*. *E. coli* is useful as a heterologous expression system for testing glyphosate resistant enzymes. The EPSP synthase mature protein-coding regions isolated from the glyphosate tolerant and glyphosate sensitive *E. indica* biotypes, can be directly compared for their ability to confer tolerance to glyphosate in transgenic hosts. *E. coil* (strain SR481) are transformed with the glyphosate resistant EPSPS gene (Ei.EPSPS:glyR) and the glyphosate sensitive EPSPS gene (Ei.EPSPS:glyS) purified from *E. indica*. The growth rate differentials of transformed cell lines grown in the presence of glyphosate contained in the culture medium is used as a measure of the resistance of the EPSPS enzyme to the inhibitory effects of glyphosate (Rogers et al., Appl. Enviro. Microbiol. 46:37–43 (1983). An appropriate *E. coli* expression vector that carries the native promoter and operator sequence from the *E. coli* lac operon (Dickson et al., Science 187:27–35 (1975) including the sequence

5'-AGATCTCCTAGGGCTTAATTAATTAAGCACTAGTCACACAGGAGGTAATTCATATG-3'  (SEQ ID NO:8)

is contained in pMON45337. This nucleotide sequence includes 1) flanking BglII and Nde1 endonuclease sites, 2) a ribosome binding site, and 3) an unstructured region 5' to the ribosome binding element (Balbas, P. et. al., in "Methods in Enzymology" (D. V. Goeddel, ed.)185: 15–37, 1990). This was inserted by ligation to facilitate expression and cloning at the ATG start codon of an open reading frame. A multiple cloning site is positioned immediately downstream of this Nde1 site, followed by the rho-independant transcriptional terminator element of the *E. coli* trpA gene (T. Sato et al., J. Biochem. (Tokyo), 101:525–534, (1987). This vector when it operbly contains the EPSP synthase coding sequences of the present invention is employed for the inducible expression of glyphosate resistant and glyphosate sensitive EPSP synthase cDNAs in *E. coli*. Other commercially available inducible *E. coli* expression vectors are suitable for testing the EPSP synthases from *E. indica*.

DNA manipulations and transformations of *E. coli* are performed according to standard procedures (Sambrook et al., Molecular Cloning: A Laboratory Manual, Cold Spring Harbor Press (1989). To construct *E. coli* expression vectors carrying the EPSP synthase mature protein coding sequences from the tolerant and sensitive *E. indica* biotypes, the oligonucleotide primers of SEQ ID NO:9 and SEQ ID NO:10.

5'-GCAATTCCATATGGCGGGCGCGGAGGAGGTGGTGCT-3'  (SEQ ID NO:9)

5'-GACTAGGAATTCTTAGTTCTTTTGACGAAAGTGCTCAGCACGTCGAAG-3',  (SEQ ID NO:10)

Figure 5:
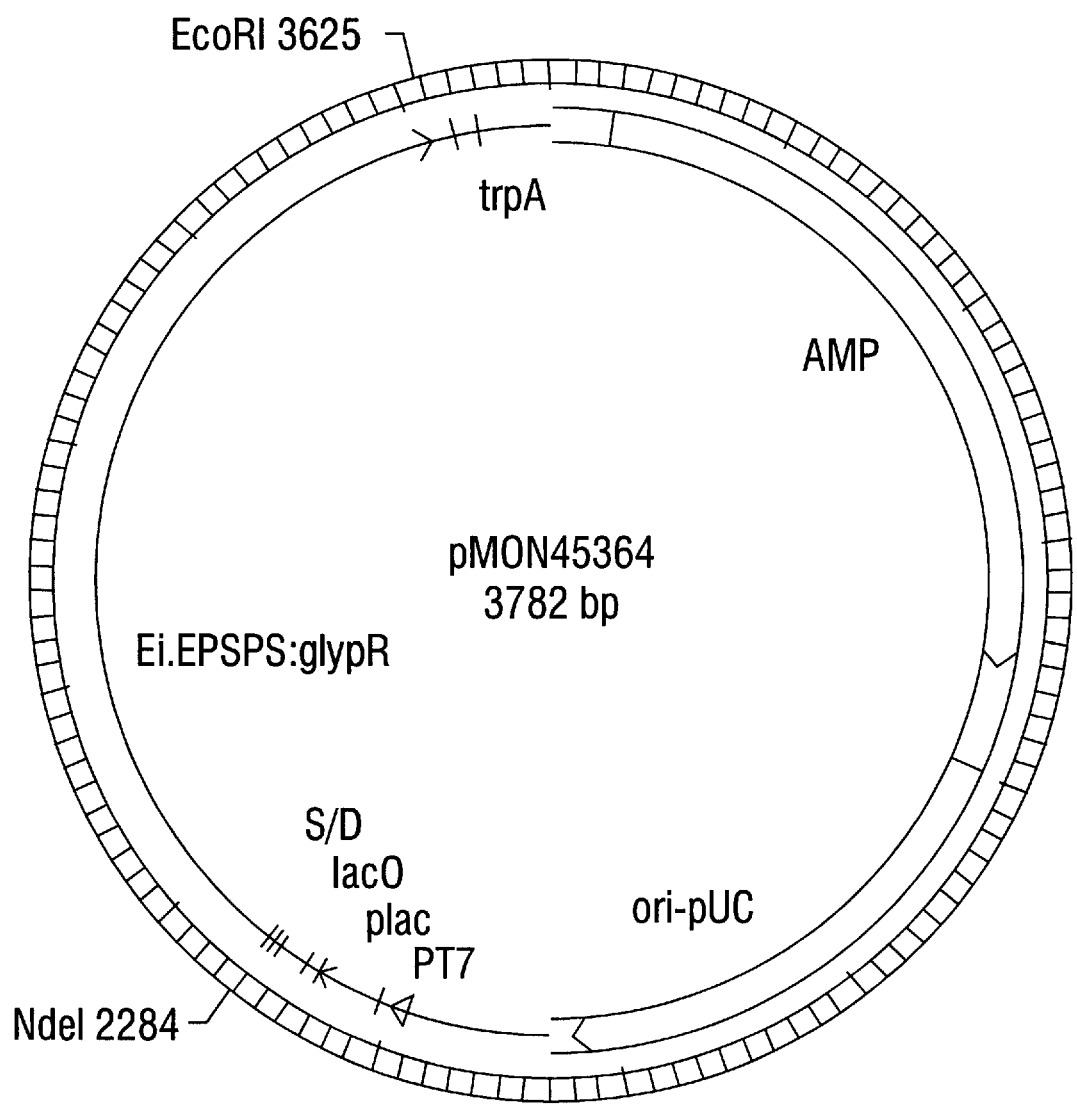
FIG. 5. Plasmid map of pMON45364.
Figure 6:
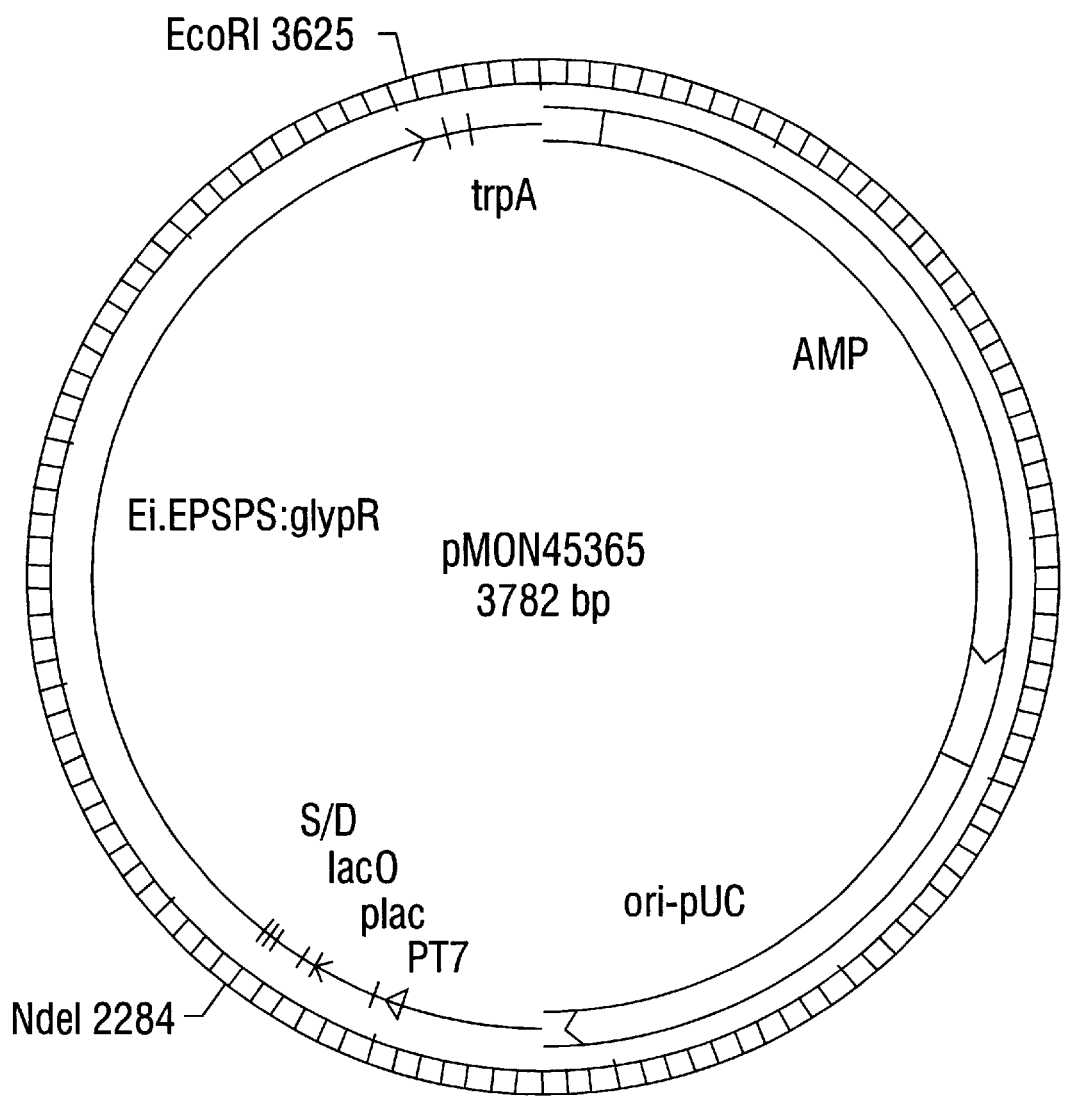
FIG. 6. Plasmid map of pMON45365.

These sequences are employed in RT-PCR reactions to generate expression cassettes suitable for cloning into pMON45337 cut with the restriction enzymes Nde1 and EcoR1. RT-PCR reactions are performed with total RNAs extracted from frozen crown samples using the RNeasy Plant Mini Kit (cat.#74904, Qiagen Inc., Valencia, Calif.) per manufacturer's instructions. Oligo dT-primed first-strand cDNAs are prepared from 5 μg samples of total RNA using the Superscript Pre-Amplification System (cat.#18089-011, Life Technologies, Rockville, Md.) per manufacturer's instructions. Two μl of first-strand cDNA are then used to generate *E. indica* EPSP synthase expression cassettes via polymerase chain reaction. The oligonucleotides are added in 50 μl RT-PCR reactions at a final concentration of 0.4 μM. PCR amplifications are then performed using the Expand High Fidelity PCR System (cat.#1 732 641, Roche Molecular Biochemicals, Indianapolis, Ind.) per manufacturer's instructions, using a thermal profile of 94° C. for 30 seconds, then 57° C. for 2 minutes, followed by 75° C. for 3 minutes, for a total of 35 cycles. The resulting PCR products are digested with Nde I and EcoRI, then ligated into pMON45337, resulting in the *E. coli* expression vectors pMON45364 (FIG. 5) and pMON45365 (FIG. 6), which contain the mature protein coding region for *E. indica* EPSP synthase isolated from the resistant and sensitive biotype, respectively. Expression of the two enzymes in *E. coli* will thus be directed by the Lac operon and trpA gene genetic elements described above for pMON45337. The accuracy of the cloned sequences are confirmed by DNA sequence analysis (ABI Prism™ 377, Perkin Elmer, Foster, Calif.). pMON45337, pMON45364, and pMON45365 are all transformed into the *E. coli* strain SR481, an aroA-strain lacking endogenous EPSP synthase activity (Padgette et al., Arch. Biochem. Biophys. 258:564–573 (1987).

Figure 3B:
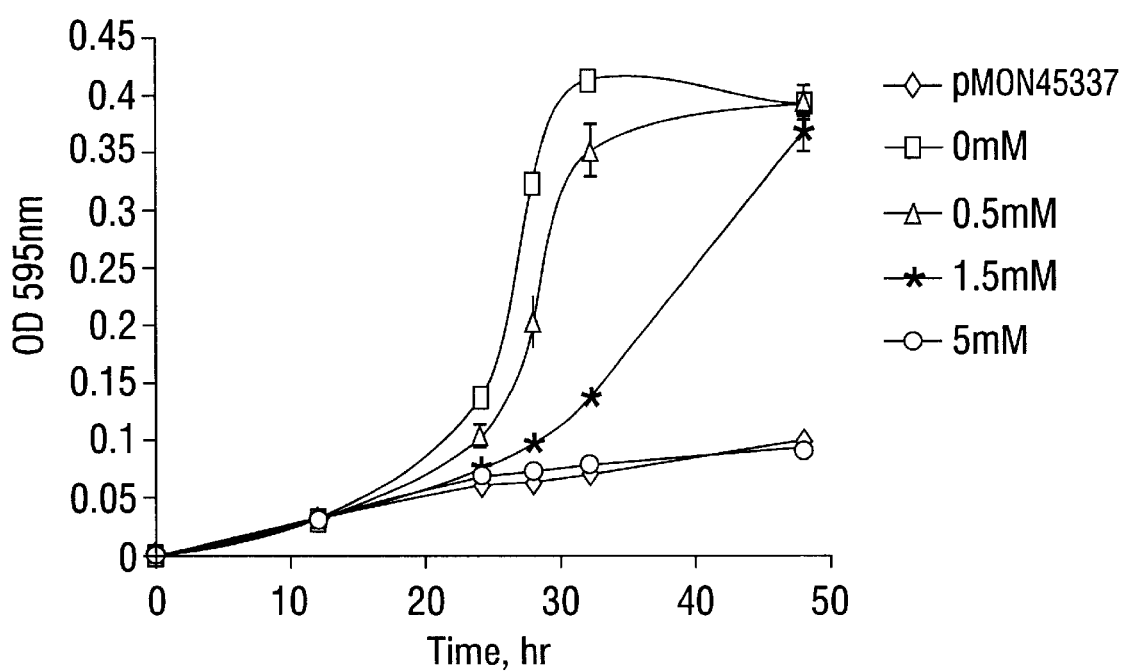

To directly compare the glyphosate tolerance of *E. coli* aroA-cells expressing the EPSP synthase gene isolated from the glyphosate sensitive *E. indica* biotype with cells expressing the EPSP synthase gene isolated from the glyphosate tolerant biotype, growth rates are compared for the two cell lines in the presence of increasing concentrations of glyphosate (FIG. 3). Growth rates are also monitored for *E. coli* SR481 cells transformed with pMON45337 (empty vector) in the absence of glyphosate as a negative control. Fresh overnight cultures of *E. coli* SR481 cells transformed with pMON45337, pMON45364 (Ei.EPSPS:glypR), and pMON45365 (Ei.EPSPS:glypS) are grown in Terrific Broth (Sambrook et al., Molecular Cloning: A Laboratory Manual, Cold Spring Harbor Press (1989), supplemented with 1.0 mM IPTG, 50 µg/ml ampicillin, and 100 µg/ml each of L-phenylalanine, L-tyrosine, and L-tryptophan. O.D.$_{595}$ measurements are taken on all of the overnight cultures to confirm similar cell densities. For *E. coli* SR481-pMON45364 and SR481-pMON45365 cells, 14 ml culture tubes (cat.#60818-725, VWR Scientific, West Chester, Pa.) each containing 3.0 ml of minimal M9 media (Sambrook et al., Molecular Cloning: A Laboratory Manual, Cold Spring Harbor Press (1989) supplemented with 50 µg/ml ampicillin, 1.0 mM IPTG, and either 0.0, 0.5, 1.5, or 5.0 mM glyphosate (N-phosphonomethyl glycine or a salt thereof) are inoculated with 100 µl of undiluted overnight culture per tube. Each experimental condition is performed in triplicate to confirm the reproducibility of the experiment. Where t=0, 12, 24, 28, 32, and 48 hours past the onset of growth in minimal media, 100 µl aliquots from each tube are removed and O.D.$_{595}$ measurements are taken immediately. A typical result from these analyses is shown in FIG. 3, where an approximately three-fold increase in tolerance to glyphosate is observed due to the expression of the EPSP synthase enzyme from the glyphosate tolerant *E. indica* biotype.

EXAMPLE 3

Kinetic characterization of the *E. indica* glyphosate-resistant EPSP synthase activity in plant and bacterial extracts. Kinetic characterization of the glyphosate-resistant *E. indica* enzyme are performed using both partially purified plant extracts as well as bacterial extracts prepared from cells expressing the cloned sequence on a suitable vector such as pMON45365. Parameters that describe the enzyme's resistance to glyphosate-mediated inhibition and the affinity for the substrate phosphoenolpyruvate (PEP) are of particular interest, given that glyphosate is a competitive inhibitor of EPSP synthase with respect to PEP (Boocock, M. et al., FEBS Letts. 154:127–133 (1983).

Preparation of extracts and radiometric EPSP synthase assays are performed using methods adapted from published procedures (Padgette et al., J. Biol. Chem. 266:22364–22369 (1991). Crown regions are dissected from whole plants, pulverized under liquid nitrogen with a mortar and pestle, then stored at −80° C. prior to extraction. Homogenates are prepared from 0.5 g tissue per sample in 25 ml extraction buffer (100 mM TrisCl, 10% glycerol, 1 mM EDTA, 1 mM benzamidine, 1 mM dithiothreitol, 1 mM 4-(2-aminoethyl)-benzenesulfonyl floride HCl, 0.1 mM leupeptin, pH 7.4) at 4° C. using a model PT3000 Polytron homogenizer (Brinkman Instuments Inc., Westbury, N.Y.). Debris is removed by 0.2 µm filtration, then the resulting supernatant is concentrated and desalted using an Ultrafree-15 centrifugal filtration unit (cat.#UFV2-BGC-10, Millipore Corp., Bedford, Mass.). Final sample volumes are approximately 0.5 ml. Protein concentrations are determined spectrophotometrically using the Bio-Rad protein assay reagent (cat.#500-0006, Bio-Rad Laboratories, Hercules, Calif.). EPSPS specific activities are determined by assaying 10 µl extract at 25° C. for 5–15 min. (50 µl reactions include 50 mM HEPES, pH 7.0, 5 mM potassium fluoride, 1 mM shikimate-3-phosphate, 0.5 mM [1-$^{14}$C]-phosphoenolpyruvate (29.0 mCi/mmol cyclohexylammonium salt; #CFQ10004, Amersham Life Science, Inc., Arlington Heights, Ill.), and 0.1 mM ammonium molybdate). Reactions are quenched with the addition of 50 µl 9:1 ethanol: 0.1 M acetic acid. Thirty µl of quenched reaction is then injected onto a Synchropak AX100 anion exchange column (cat.#942804, P. J. Cobert Associates, Inc., St. Louis, Mo.) equilibrated with 0.235 M potassium phosphate buffer, pH 6.5, and eluted isocratically with the same buffer. A model D525 radioactive flow detector (Packard Instrument Co., Downer's Grove, Ill.) is used to determine production of [$^{14}$C]-EPSP in the reaction.

Figure 4:
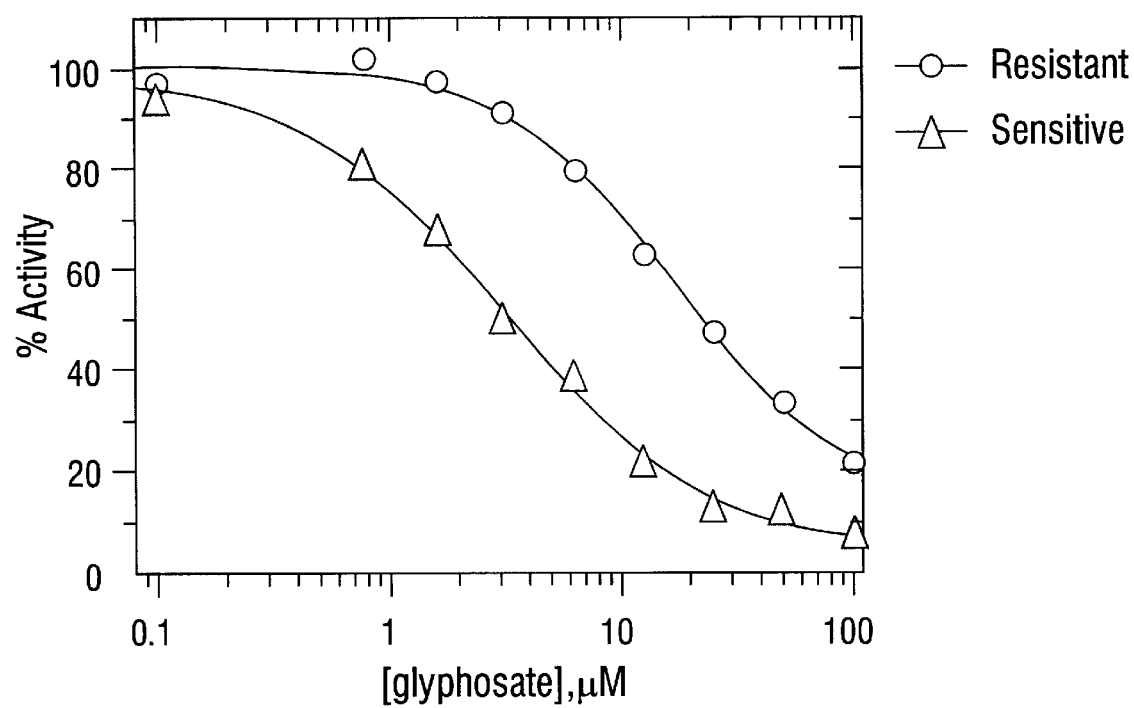
FIG. 4. Glyphosate inhibition study comparing the EPSP synthase activities detectable in extracts prepared from the glyphosate-sensitive and tolerant *E. indica* biotypes.

For determination of $I_{50}$ (glyphosate) values, the assays as described, are performed in the presence of increasing concentrations of glyphosate and the resulting activities analyzed and plotted using GraFit version 3.0 software (Erithacus Software Ltd., Staines, U.K.). FIG. 4 shows data generated for a typical glyphosate inhibition study, comparing the EPSP synthase activities detectable in extracts prepared from the glyphosate sensitive and tolerant *E. indica* biotypes. These data demonstrate the difference in sensitivity to glyphosate for the activities present in the two biotypes, with the sensitive biotype EPSPS activity having an $I_{50}$ (glyphosate) of approximately 3.0 µM and the tolerant biotype EPSPS approximately 16 µM.

Activities of the enzymes extracted from several different tolerant and sensitive *E. indica* individuals are compared in the presence and absence of 1.6 µM glyphosate (Table 1), showing similar sensitivity to glyphosate and very low plant-to-plant variation exhibited among individuals from the same biotype.

TABLE 1

Percent-maximal EPSPS activity in extracts from different *E. indica* individuals assayed in the presence 1.6 uM glyphosate

| biotype-individual | EPSPS Activity, (% maximal @ 1.6 uM glyphosate) |
|---|---|
| Sensitive-#1 | 51.6 |
| Sensitive-#2 | 55.6 |
| Sensitive-#3 | 57.4 |
| Tolerant-#1 | 76.3 |
| Tolerant-#2 | 86.0 |
| Tolerant-#3 | 82.4 |

Similar analyses are performed using extracts prepared from *E. coil* strain SR481 cells expressing the cloned *E. indica* sensitive and resistant EPSPS enzymes from the expression vectors pMON45365 and pMON45364, respectively. Fresh bacterial overnight cultures are grown at 37° C. in Terrific Broth, (Sambrook et al., Molecular Cloning: A Laboratory Manual, Cold Spring Harbor Press (1989), supplemented with 50 µg/ml ampicillin and 100 µg/ml each of L-phenylalanine, L-tyrosine, and L-tryptophan. Overnight cultures are used to inoculate large-scale cultures containing the same media at a 1:100 dilution, then grown to an $O.D._{595}$ of 0.6 at 37° C. with vigorous shaking. The culture is inducted by the addition of IPTG to 1.0 mM final concentration then incubation is continued for an additional 4 hours. Cells are then pelleted by centrifugation at 10,000×g for 5 minutes, then washed twice in ice-cold 0.9% NaCl. Excess wash buffer is removed by aspiration, then pellets are flash-frozen in liquid nitrogen and stored at −80° C. prior to use. Bacterial extracts are prepared using the same extraction buffer used for plant extracts, with 3 ml buffer added per gram of pelleted cells. Cells are lysed using a French press (model #J5-598A, American Instrument Co., Silver Springs, Md.), then extracts are centrifuged at 14,000×g for 10 minutes to remove cell debris. The supernatants are then desalted using a PD-10 column (cat.#17-0851-01, Amersham Pharmacia Biotech Inc., Piscataway, N.J.). EPSP synthase assays are performed as described above for plant-derived extracts. Table 2 illustrates a typical result for bacterial extracts expressing the sensitive and resistant E. indica EPSP synthase enzymes assayed in the presence and absence of 1.6 µM glyphosate. These data indicate that similar inhibition kinetics are obtained when these results are compared to the respective activities detected in plant extracts.

TABLE 2

EPSPS activity in aroA-bacterial extracts transformed with pMON45364 or pMON45365 assayed in the presence and absence of glyphosate

| sample | activity (nMol/min/mg protein) | % maximal activity (1.6 uM glyphosate) |
|---|---|---|
| SR481(pMON45364) | | |
| − glyphosate | 34.3 | |
| + glyphosate | 24.9 | 72.6 |
| SR481(pMON45365) | | |
| − glyphosate | 27.1 | |
| + glyphosate | 14.4 | 53.1 |

EXAMPLE 4

Figure 7:
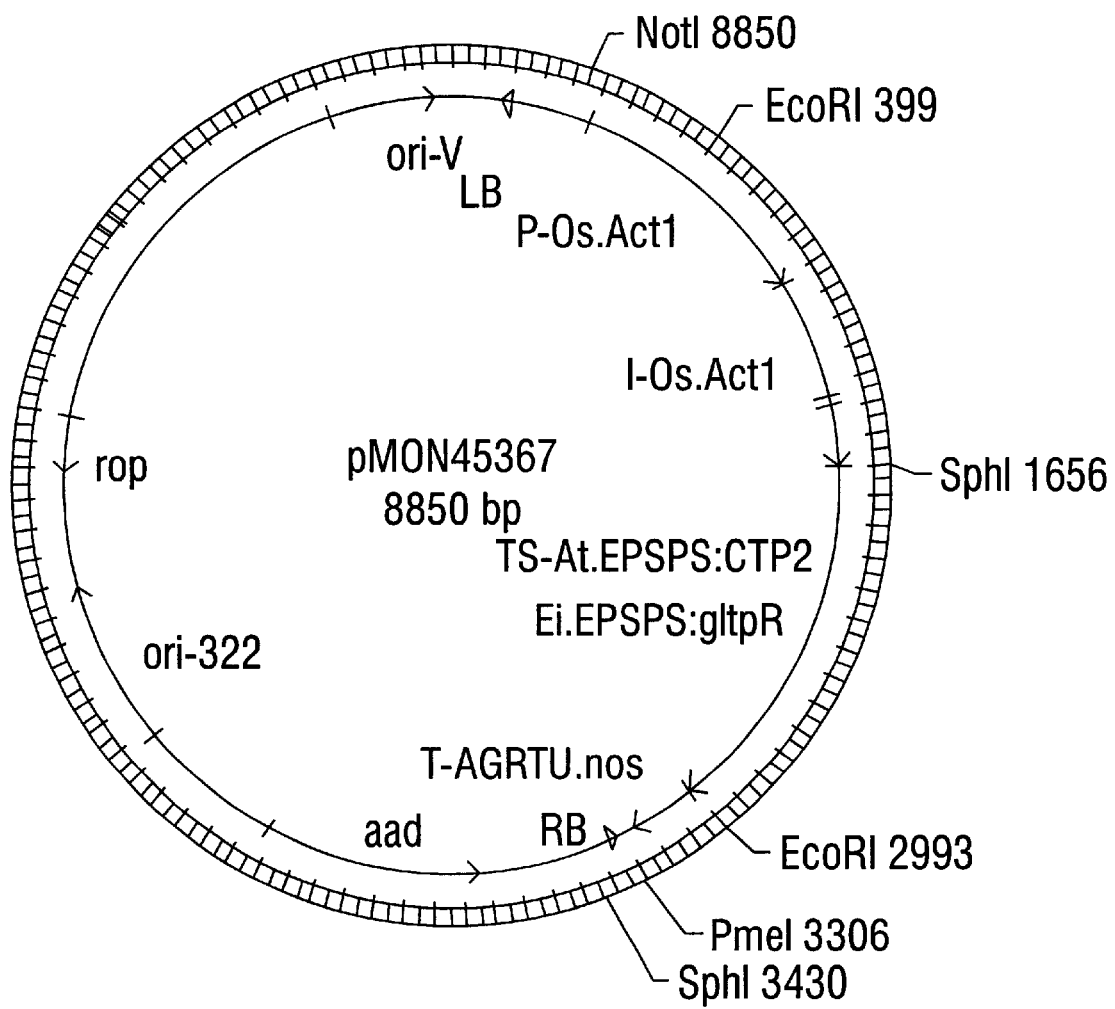
FIG. 7. Plasmid map of pMON45367.
Figure 8:
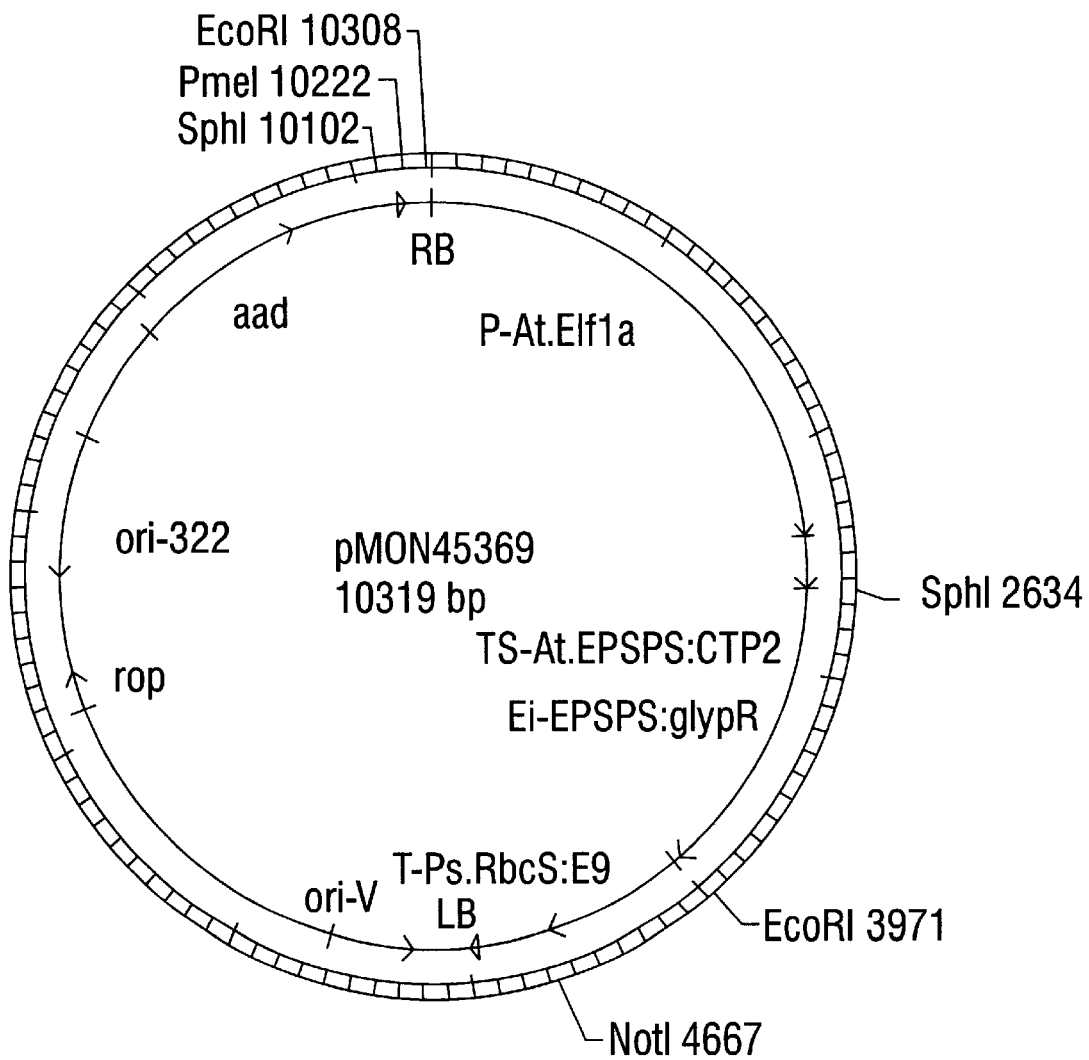
FIG. 8. Plasmid map of pMON45369.

The use of the glyphosate resistant EPSP synthase gene from E. indica (Ei.EPSPS:glypR) to develop glyphosate tolerant crop plants involves the construction of plant transformation vectors that include the appropriate combination of genetic elements necessary to direct adequate expression levels in target tissues. For monocotyledonous crop plants, a monocot vector that utilizes a plant expression cassette that contains a promoter (P) and first intron (I) from the rice (Os) actin gene (P-Os.Act1/I-Os.Act1 (U.S. Pat. No. 5,641,876), plastid transit peptide sequence (TS) from the Arabidopsis thaliana* (At) EPSP synthase gene (TS-At.EPSPS:CTP) (Klee et al. Mol. Gen. Genet. 210:437–442), a *E. indica* glyphosate resistant EPSPS coding sequence, and the polyadenylation/termination (T) region from the *Agrobacterium tumefaciens* nopaline synthase gene (T-AGRTU.nos), would be an appropriate choice. This expression cassette may be combined with a second transgene expression cassette by plant breeding, plant transformation, or by joining in a DNA construct that comprises a plant DNA virus promoter, for example, the cauliflower mosaic virus (CaMV) 35S promoter containing a tandem duplication of the enhancer region, operably connected to a *Zea mays* Hsp70 intron, operably connected to a nucleic acid sequence encoding an *Arabidopsis thaliana* EPSPS chloroplast transit peptide sequence, operably connected to a *E. indica* glyphosate resistant EPSPS coding sequence, operably connected to a nopaline synthase transcriptional terminator. Other combinations of genetic elements are known and those skilled in the art of plant molecular biology can easily construct plant expression vectors that will express the *E. indica* EPSPS glyphosate resistant enzyme at sufficient levels to confer glyphosate the transformed plant.

For specific dicotyledonous species, a plant expression vector that utilizes the promoter and 5' untranslated region (including intron I) of the plant elongation factor 1α gene (Elfα-A1) as described in U.S. Pat. No. 5,177,011 or more specifically, dicot vector of the present invention which utilizes the *Arabidopsis thaliana* Elfα-A1 promoter and intron sequence (P-At.Elf1a/I-At.Elf1a), (Axelos et al., Mol. Gen. Genet. 219: 106–112 (1989); Genbank accession #U63815), the chloroplast transit peptide from the *Arabidopsis thaliana* EPSP synthase gene (TS-At.EPSPS:CTP2), and the polyadenylation/3' termination region from the *Pisum sativum* ribulose-1,5-bisphosphate carboxylase gene (T-Ps.RbcS:E9). This expression cassette may be combined with a second transgene expression cassette by plant breeding, plant transformation, or by joining in a DNA construct that comprises a plant DNA virus promoter, for example, the Figwort mosaic virus (FMV) 34S promoter, operably connected to a nucleic acid sequence encoding an *Arabidopsis thaliana* EPSPS chloroplast transit peptide sequence, operably connected to a *E. indica* glyphosate resistant EPSPS coding sequence, operably connected to a nopaline synthase transcriptional terminator. Other combinations of genetic elements are known and those skilled in the art of plant molecular biology can easily construct plant expression vectors that will express the *E. indica* EPSPS glyphosate resistant enzyme at sufficient levels to confer glyphosate tolerance to the transformed plant.

To construct monocotyledonous and dicotyledonous plant expression vectors carrying the DNA encoding the EPSP synthase mature protein coding sequence isolated from the glyphosate tolerant *E. indica* biotype (SEQ ID NO. 6, FIG. 1), the oligonucleotide primers of SEQ ID NO: 11 and SEQ ID NO: 12 are employed in PCR reactions to generate an expression cassette suitable for direct cloning into a monocot vector and a dicot vector.

```
5'-GCAATTCGCATGCCGGGCGCGGAGGAGGTGGTGCT-3'            (SEQ ID NO:11)

5'-GACTAGGAATTCTTAGTTCTTTTGACGAAAGTGCTCAGCACGTCGAAG-3' (SEQ ID NO:12)
```

The PCR reactions are performed using 300–500 ng of pMON45364 plasmid DNA as template to amplify the *E. indica* EPSP synthase mature protein coding region, flanked by Sph1 and EcoR1 restriction cleavage sites. The oligonucleotides are added in 50 μl PCR reactions at a final concentration of 0.4 µM. PCR amplifications are then performed using the Expand High Fidelity PCR System (cat.#1 732 641, Roche Molecular Biochemicals, Indianapolis, Ind.) per manufacturer's instructions, using a thermal profile of 94° C. for 30 seconds, then 57° C. for 2 minutes, followed by 75° C. for 3 minutes, for a total of 20–35 cycles. The resulting PCR products are digested with Sph1 and EcoR1, then ligated into pMON45366 and pMON45368 resulting in the plant expression vectors pMON45367 (FIG. 7) and pMON45369 (FIG. 8), respectively. The accuracy of the cloned sequences are confirmed by DNA sequence analysis (ABI Prism™ 377, Perkin Elmer, Foster City, Calif.).

EXAMPLE 5

Transgenic corn can be produced by particle bombardment transformation methods as described in U.S. Pat. No. 5,424,412. The plant expression vector (pMON45367) contains the glyphosate resistant *E. indica* EPSPS mature protein coding sequence in an expression cassette suitable for expression in monocot plants. The pMON45367 plasmid DNA is digested with Not1 and Pme1 restriction endonucleases to complete digestion. The 3.3 kb expression cassette is agarose gel purified, then bombarded into embryogenic corn tissue culture cells using a Biolistic® (Dupont, Wilmington, Del.) particle gun with purified isolated DNA fragment. Transformed cells are selected on glyphosate (N-phosphonomethyl glycine and its salts) containing media and whole plants are regenerated then grown under greenhouse conditions. Fertile seed is collected, planted and the glyphosate tolerant phenotype is back crossed into commercially acceptable corn germplasm by methods known in the art of corn breeding (Sprague et al., Corn and Corn Improvement 3$^{rd}$ Edition, Am. Soc. Agron. Publ (1988).

Transgenic corn plants can be produced by an Agrobacterium mediated transformation method. A disarmed Agrobacterium strain C58 (ABI) harboring a binary vector (pMON45367) is used for all the experiments. The pMON45367 is transferred into Agrobacterium by a triparental mating method (Ditta et al., Proc. Natl. Acad. Sci. 77:7347–7351). Liquid cultures of Agrobacterium are initiated from glycerol stocks or from a freshly streaked plate and grown overnight at 26° C.–28° C. with shaking (approximately 150 rpm) to mid-log growth phase in liquid LB medium, pH 7.0 containing 50 mg/l kanamycin, 50 mg/l streptomycin and spectinomycin and 25 mg/l chloramphenicol with 200 µM acetosyringone (AS). The Agrobacterium cells are resuspended in the inoculation medium (liquid CM4C) and the density is adjusted to $OD_{660}$ of 1. Freshly isolated Type II immature HiIIxLH198 and Hill corn embryos are inoculated with Agrobacterium containing pMON45367 and co-cultured 2–3 days in the dark at 23° C. The embryos are then transferred to delay media (N6 1-100-12/micro/Carb 500/20 µM AgNO3) and incubated at 28° C. for 4 to 5 days. All subsequent cultures are kept at this temperature. Coleoptiles are removed one week after inoculation. The embryos are transferred to the first selection medium (N61-0-12/Carb 500/0.5 mM glyphosate). Two weeks later, surviving tissue are transferred to the second selection medium (N61-0-12/Carb 500/1.0 mM glyphosate). Subculture surviving callus every 2 weeks until events can be identified. This will take 3 subcultures on 1.0 mM glyphosate. Once events are identified, bulk up the tissue to regenerate. For regeneration, callus tissues are transferred to the regeneration medium (MSOD 0.1 µM ABA) and incubated for two weeks. The regenerating calli are transferred to a high sucrose medium and incubated for two weeks. The plantlets are transferred to MSOD media in culture vessel and kept for two weeks. Then the plants with roots are transferred into soil.

Three $R_0$ plants are regenerated for any given transgenic event. These three plants are expected to be near isogenic because they are thought to be derived from a single transgenic plant cell. Thus, one plant is used as a non-sprayed control and the remaining two plants are treated with glyphosate (as Roundup® herbicide). Plants are most effectively treated with glyphosate at V2–V6 stage. Glyphosate (as Roundup® herbicide) is administered through the use of a linear track sprayer set to deliver a 16, 32 or 64 oz./A rate of glyphosate. Vegetative tolerance to the glyphosate is visually evaluated a week after spray based on a scale of 0 to 5 (0=No observable/vegetative effect of glyphosate; 1=Chlorosis observed; 2=Advanced chlorosis, minor necrosis; 3=Advanced chlorosis, moderate necrosis; 4=Advanced chlorosis, severe necrosis; 5=No live tissue remaining). The $R_0$ plants produced are allowed to self, then $R_1$ plants are screened using spray applications of glyphosate and the rating system as described for the $R_0$ screen. An increase in whole-plant tolerance to the herbicide, as compared to non-transgenic control plants, is used to assess the utility of the *E. indica* EPSP synthase enzyme for the generation of glyphosate tolerance in planta.

EXAMPLE 6

Immature embryos of wheat (*Triticum aestivum* L) cultivar Bobwhite are isolated from the immature caryopsis 13–15 days after pollination, and cultured on CM4C (Table 3) for 3–4 days. The embryos showing active cell division, but no apparent callus formation are selected for Agrobacterium infection.

TABLE 3

| Supplemental Components in Basal Media[1] | | | | |
| --- | --- | --- | --- | --- |
| Components | CM4 | CM4C | MMS.2C | MMS0 |
| 2,4-D (mg/l) | 0.5 | 0.5 | 0.2 | — |
| Pichloram (mg/l)[2] | | 2.2 | 2.2 | |
| Maltose (g/l) | 40.0 | 40.0 | 40.0 | 40.0 |
| Glutamine (g/l) | | 0.5 | 0.5 | |
| Magnesium Chloride (g/l) | | 0.75 | 0.7 | |
| Casein Hydrolysate (g/l) | | 0.1 | 0.1 | |
| MES (g/l) | | 1.95 | 1.95 | 1.95 |
| Ascorbic Acid (mg/l)[2] | | 100.0 | 100.0 | 100.0 |
| Gelling Agent (g/l)[3] | 2(P) | 2(P) | 2(G) | 2(G) |

[1]All media contain basal salts (MS basal salts) and vitamins (MS vitamins) from Murashige and Skoog (1962). The pH in each medium is adjusted to 5.8.
[2]Filter-sterilized and added to the medium after autoclaving.
[3]Phytagel ™ (P) or Gelrite ® (G).

A disarmed Agrobacterium strain C58 (ABI) harboring a binary vector of interest (pMON45367) is used for all the experiments. The pMON45367 is transferred into Agrobacterium by a triparental mating method (Ditta et al., Proc. Natl. Acad. Sci. 77:7347–7351). Liquid cultures of Agrobacterium are initiated from glycerol stocks or from a freshly streaked plate and grown overnight at 26° C.–28° C. with shaking (approximately 150 rpm) to mid-log phase ($OD_{660}$=1–1.5) in liquid LB medium, pH 7.0 containing 50 mg/l kanamycin, 50 mg/l streptomycin and spectinomycin and 25 mg/l chloramphenicol with 200 µM acetosyringone (AS). The Agrobacterium cells are resuspended in the inoculation medium (liquid CM4C) and the density is adjusted to $OD_{660}$ of 1. The immature embryos cultured in CM4C medium are transferred into sterile petri plates (16×20 mm) or wells of a 6-well cell culture plate (Costar Corporation, Cambridge, Mass.) containing 10 ml of inoculation medium per petri plate or 5 ml per cell culture cluster plate. An equal amount of the Agrobacterium cell suspension is added such that the final concentration of Agrobacterium cells is an $OD_{600}$ of 0.5. In most experiments, pluronic F68 is added to the inoculation mixture at a final concentration of 0.01%. The ratio between the Agrobacterium and immature embryos is about 10 ml: 20–200 IEs. The inoculation is allowed to proceed at 23° C.–26° C. from 5–60 minutes.

After the inoculation period, the remaining Agrobacterium cells are removed from the explants by using vacuum aspiration equipment. A piece of sterile Whatman No. 1 filter paper (to fit the size of the petri plate) is placed in each of 60×15 or 60×20 mm petri dishes. Two hundred µl of sterile water is placed in the middle of the filter paper. After 2–3 minutes, the inoculated immature embryos are placed in the plates. Usually, 20–50 explants are grouped as one stack (about 1 cm in size and 60–80 mg/stack), with 4–5 stacks on each plate. The plates are immediately covered with Parafilm® and then co-cultivated in the dark at 24° C.–26° C. for 2–3 days.

The co-cultivated PCIEs are transferred CM4C+500 mg/l carbenicillin medium (delay medium) at dark. After 7 days on the delay medium, the immature embryos are transferred to CM4C supplemented with 2 mM glyphosate and 500 mg/l carbenicillin for selection for one week. Then calli are transferred to MMS0.2C+0.1 mM glyphosate+250 mg/l carbenicillin medium for 2 weeks under light for further selection. Embryogenic calli are transferred to a second regeneration medium MMS0C with lower glyphosate concentration (0.02 mM) and 500 mg/L carbenicillin for plant regeneration. Those embryogenic calli are transferred onto fresh medium every two weeks. Regenerated plantlets are transferred to Sundae cups (Sweetheart Cup Company, Chicago, Ill.) containing the second regeneration medium for further growth and selection. When roots are well established from transgenic plants the plants are transferred to soil for further evaluation.

EXAMPLE 7

Figure 9:
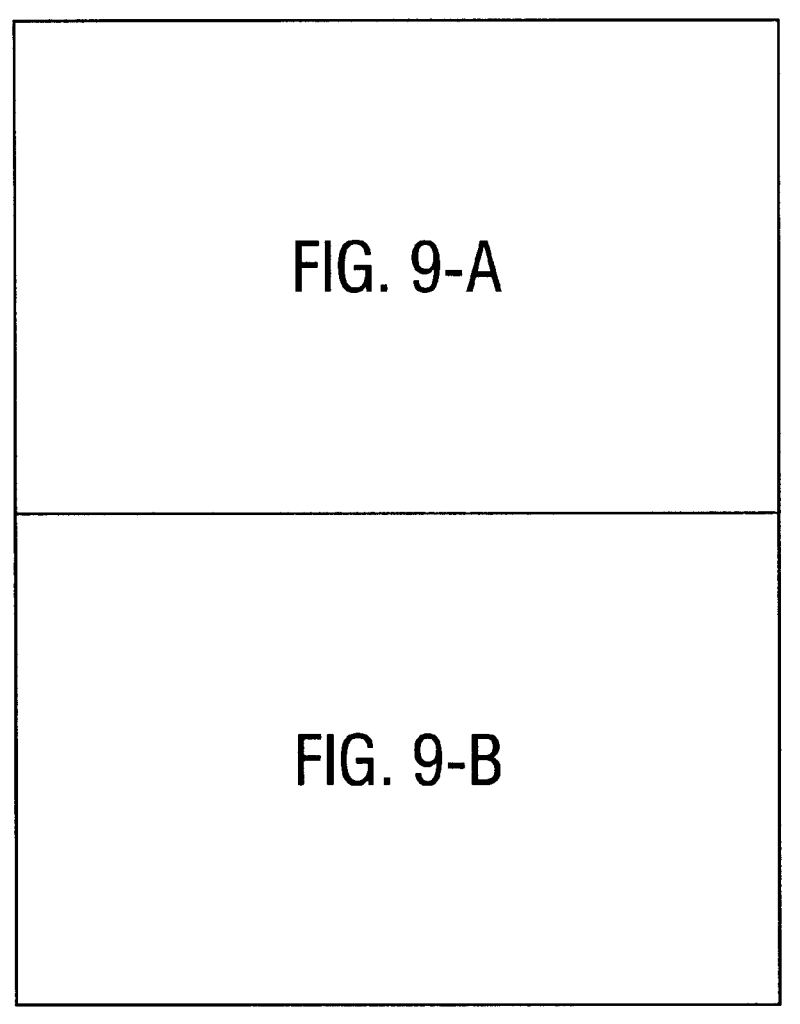

Novel glyphosate-resistant EPSP synthases can be designed based on the *E. indica* glyphosate resistant EPSPS. The amino acid sequence deduced from the cDNA sequence shows that two amino acid substitutions distinguish the mature EPSP protein sequence derived from the glyphosate-tolerant *E. indica* biotype (top row, FIG. 9) from that of the glyphosate sensitive *E. indica* biotype EPSPS protein sequence (bottom row, FIG. 9). The substitution of a serine for a proline at position 107 of the *E. indica* EPSPS amino acid sequence and in the corresponding amino acid position in both higher plant and bacterial EPSP synthase enzymes is known to result in the enzyme having resistance to glyphosate (Padgette et al., J. Biol. Chem. 266:22364–22369 (1991); U.S. Pat. No. 4,535,060). All catalytic domain single amino acid substitution EPSP synthase variants characterized to date that exhibit increased tolerance to glyphosate have a higher $K_i$ for glyphosate, but also have an increase in the apparent $K_m$ for PEP and reduced $V_{max}$, thereby lowering the catalytic efficiency ($V_{max}/K_m$) of the enzyme (Kishore et al., Annu. Rev. Biochem. 57:627–663 (1988); glyphosate (Padgett et al., J. Biol. Chem. 266:22364–22369 (1991). In contrast, the *E. indica* glyphosate resistant EPSP synthase (*E. indica* glypR) exhibits a high affinity for PEP, while retaining significant catalytic efficiency in the presence of glyphosate (TABLE 4). The engineered petunia (*Petunia hybrida*) and corn (*Zea mays*) glyphosate resistant (glypR) variants that in studies by others (U.S. Pat. No. 5,866,774; U.S. Pat. No. 6,040,497) have shown to confer a high level of glyphosate tolerance in transgenic plants were assayed for affinity for PEP and inhibition by glyphosate. All of the naturally occurring wild type (wt) *Z. mays* glyphosate sensitive (*Z. mays* glypS), wild type *P. hybrida* glyphosate sensitive (*P. hybrida* glypS) and the *E. indica* glypS and *E. indica* glypR wild type EPSPS enzymes have very similar $K_m$ values for PEP. The single amino acid substitutions engineered into the catalytic domain of *P. hybrida* EPSPS enzyme drastically increases the $K_m$ for PEP. The single amino acid substitution found in this domain in the naturally occurring variant of *E. indica* glypR was found to not have a major effect on the $K_m$ indicating that this enzyme will continue to function well in the plant chloroplast. It required a double mutation in the *Z. mays* EPSPS enzyme to achieve a low $K_m$ for PEP.

TABLE 4

Comparison of the apparent $K_m$ for PEP and apparent $K_i$ for glyphosate of the *E. indica* glyphosate resistant EPSPS with other known plant EPSPS modified for glyphosate resistance.

| EPSPS enzyme | $K_m$PEP (µM) | $K_i$ Glyphosate (µM) |
|---|---|---|
| *E. indica* glypS | 5 | 0.05 |
| *E. indica* glypR (Pro-Ser) | 7 | 1 |
| *Z. mays* glypS (wt) | 5 | 0.2 |
| *Z. mays* glypR (Thr-Ile, Pro-Ser) | 5 | 60 |
| *P. hybrida* glypS (wt) | 5 | 0.4 |
| *P. hybrida* glypR (Pro-Ser) | 44 | 3 |
| *P. hybrida* glypR (Gly-Ala) | 200 | 2000 |
| *P. hybrida* glypR (Gly-Ala, Pro-Ser) | 340 | 8500 |

$K_m$(PEP) determinations for the different enzymes are performed at saturating shikimate-3-phosphate (S3P) concentrations, which is determined according to standard methods (Fersht, *Enzyme Structure and Mechanism*, W. H. Freeman and Co., Ltd., San Francisco, Calif., 1977). A series of PEP concentrations are tested, such that the final range of concentrations spans one order of magnitude above and below the experimentally determined $K_m$. $K_i$ (glyphosate), with respect to PEP, is determined in a similar manner, at saturating S3P concentrations, except that velocity vs. [PEP] is determined for a range of glyphosate concentrations (Orsi in "Methods in Enzymology" (Purich, ed.), vol. 63, pg. 159–183, 1979). Calculations, graphical representation, and statistical analysis of enzyme kinetic data are performed using GraFit version 3.0 software (Erithacus Software Ltd., Staines, U.K.).

It is anticipated by this study that transgenic plants resistant to glyphosate are made by transformation with an *E. indica* glyphosate resistant EPSPS gene construct that can include additional modification of the naturally occurring amino acid sequence. These changes are be made by site-directed mutagenesis of the codons of DNA sequence to incorporate other known amino acid substitutions in glyphosate resistant plant EPSPSs, such as the threonine to isoleucine substitution at 103 (U.S. Pat. No. 6,040,497), and glycine to alanine substitution at 102 (U.S. Pat. No. 5,188,642) in the catalytic domain of the *E. indica* EPSPS amino acid seqeunce. Furthermore, it is anticipated that the catalytic domain of the *E. indica* EPSPS, as well as other plant EPSP Synthases, can be modified to the amino acid sequence of the catalytic domain of the Agrobacterium strain CP4 glyphosate resistant EPSPS (U.S. Pat. No. 5,633,435) by the same methods. This modification will result in the plant derived EPSPS possessing similar PEP binding and glyphosate resistance as the CP4 glyphosate resistant EPSPS that has been used in cotton, corn, canola, soybeans, potato, wheat, sugarbeet and other agronomically important crop plant to impart plant tolerance to glyphosate. Modification of plant EPSP Synthases to the CP4 EPSPS catalytic domain sequence may comprise the deletion of an amino acid and the substitution of other amino acids. In particular the deletion of the amino acid at 107 of the *E. indica* EPSPS sequence (FIG. 2) or the same relative amino acid position in other plant EPSP Synthases that can in addition to the deletion, include substitutions of an alanine for a glycine at 102, glycine for alanine at 104, cysteine for methionine at 105, methionine for alanine at 110, or glycine for alanine at 111. Previous random and site-directed mutations in the conserved region (catalytic domain) of bacterial and plant EPSPSs have shown that modifications that increase the $K_i$ for glyphosate while keeping the $K_m$ for PEP low are important for an enzyme that is useful for genetically modifying plants for glyphosate tolerance (U.S. Pat. No. 5,866,775).

EXAMPLE 8

*E. indica* EPSPS regulatory sequences can be isolated by any number of methods known to those of skill in the art for genomic library preparation. For genomic libraries of the present invention, *E. indica* genomic DNA is isolated by a CsCl purification protocol according to Current Protocols in Molecular Biology, ed. Ausubel et al., Greene Publishing and Wiley-Interscience, New York, 1992 (with periodic updates); or by a CTAB purification method (Rogers et al., Plant Mol. Biol., 5:69, 1988). Reagents are available commercially (see, for example Sigma Chemical Co., St. Louis, Mo.). The genomic DNA libraries are prepared according to manufacturer instructions (Genome Walker™, CloneTech Laboratories, Inc, Palo Alto, Calif.). In separate reactions, genomic DNA is subjected to restriction enzyme digestion overnight at 37° C. with the following blunt-end endonucleases: EcoRV, Sca1, Dra1, PvuII, or Stu1 (CloneTech Laboratories, Inc. Palo Alto, Calif.). The reaction mixtures are extracted with phenol:chloroform, ethanol precipitated, and resuspended in Tris-EDTA buffer (10 mM Tris-HCl, pH 8.0, 1 mM EDTA). The purified blunt-ended genomic DNA fragments are then ligated to the Genome Walker™ adapters and ligation of the resulting DNA fragments to adapters were done according to the manufacturer's protocol. After ligation, each reaction is heated treated (70° C. for 5 min) to terminate the reaction and then diluted 10-fold in Tris-EDTA buffer. One µl of each respective ligation is then amplified in a 50 µl reaction according to manufacturer's recommended protocol using an adaptor-specific oligonucleotide (supplied by manufacturer) and an *E. indica* EPSP synthase gene-specific oligonucleotide, such as SEQ ID NO 4. One µl of each primary reaction is diluted 50-fold and 1 µl of this dilution is then amplified in a secondary amplification using a "nested" adaptor-specific oligonucleotide (supplied by manufacturer) and a "nested" gene-specific oligonucleotide such as SEQ ID NO 5. PCR products, representing 5' regions of the *E. indica* EPSP synthase gene are then purified by agarose gel electrophoresis using a QIAquick Gel Extraction Kit (cat.#28704, Qiagen Inc., Valencia, Calif.) then directly cloned into the pCR2.1-TOPO vector (cat.#K4500-40, Invitrogen, Carlsbad, Calif.). The identity of the cloned PCR products is confirmed by DNA sequence analysis (ABI Prism™377, Perkin Elmer, Foster City, Calif.). The same *E. indica* Genome Walker™ libraries and methods that are used to isolate the *E. indica* EPSP synthase 5' region can be used to isolate the 3' region of *E. indica* EPSP synthase gene, by substituting gene-specific primers (first round SEQ ID NO: 13 and second round SEQ ID NO: 14) that anneal to the 3' end of the gene. Amplification products are cloned and verified as for the 5' end of the *E. indica* EPSP synthase gene.

5'-TGCAATCCGGACTGAGCTAACAAAGC-3'      (SEQ ID NO:13)

5'-ACTGCATTATCACACCGCCCGAGAAG-3'      (SEQ ID NO:14)

The translation initiation codon is determined for the *E. indica* EPSP synthase gene by inspection, anticipating an initiation codon approximately 63 codons upstream of the start of the mature protein codon region, based on comparison to the maize EPSP synthase gene. Primers are then designed to amplify approximately 2.5 kb of the 5' region beginning at the initiation codon. These primers incorporate restriction sites for cloning into expression vectors, for example, placing a EcoR1 site in the 5' end of promoter region the *E. indica* EPSP synthase gene and an Nco1site incorporating the translation start. Such primers are added in a 50 µl RT-PCR reaction at a final concentration of 25 µM with 50 ng of *E. indica* genomic DNA. PCR amplifications are then performed using the Expand High Fidelity PCR System (cat.#1 732 641, Roche Molecular Biochemicals, Indianapolis, Ind.) per manufacturer's instructions. A thermal profile of 94° C. for 30 seconds, followed by 60° C. for 30 seconds, then 72° C. for 3 minutes is used for thirty cycles. This is followed by a cycle of 72° C. for 3 minutes. The gel purified amplification product is then digested with Pst1 and Nco1.

The 3' end of the *E. indica* EPSP synthase gene is amplified using two gene specific primers (SEQ ID NO:15 and SEQ ID NO:16) which incorporate a BamH1 site immediately downstream of the translation stop codon and a Pst1 approximately 650 bases downstream of the translation stop codon. The product is amplified as for the 5' end of the *E. indica* EPSP synthase gene except an extension time of 1 minute is used. The gel purified product is digested with BamH1 and Pst1.

(SEQ ID NO:15)
5'-CTAAGGATCCTCTGTGCCTGCCTCATGAAGAGAGTT-3'

(SEQ ID NO:16)
5'-TGATCTGCAGGCAAGTGTCTTACCCTTACCCTTCTG-3'

The 5' (EcoR1/Nco1 fragment) regulatory and 3' (BamH1/Pst1 fragment) regulatory regions of the *E. indica* EPSP synthase gene can be ligated to a compatibly digested vector and a coding region to generate a transgene capable of expressing a transcript under control of *E. indica* EPSP synthase gene regulatory elements. An example of such is a coding region would be the *A. tumefaciens* strain CP4 EPSP synthase gene (U.S. Pat. No. 5,633,435) expressed under the control of the *E. indica* regulatory sequences.

The basal expression of the *E. indica* EPSP synthase gene promoter may be modified to enhance its expression. Methods known to those of skill in the art can be used to insert enhancing elements (for example, subdomains of the CaMV 35S promoter, Benfey et. al, 1990 EMBO J. 9: 1677–1684) into the *E. indica* EPSP synthase gene 5' sequence to generate a promoter which encompasses the temporal and spatial expression of the *E. indica* EPSP synthase gene but have quantitatively higher levels of expression. Similarly, tissue specific modifications of the *E. indica* EPSP synthase 5' region expression can be accomplished with elements determined to specifically activate or repress gene expression (for example, pollen specific elements, Eyal et al., 1995 Plant Cell 7: 373–384).

From the foregoing, it will be seen that this invention is one well adapted to attain all the end and object herein above set forth together with advantages that are obvious and that are inherent to the invention.

The embodiments described above are provided to better elucidate the practice of the present invention. Many possible embodiments may be made of the invention without departing from the scope thereof, it should be understood that these embodiments are provided for illustrative pur poses only, and are not intended to limit the scope of the invention.

It will be understood that certain features and subcombinations are of utility and may be employed without reference to other features and subcombinations. This is comtemplated by and is within the scope of the claims. All publications and published patent documents cited in this specification are incorporated herein by reference to the same extent as if each individual publication or patent application was specifically and individually indicated to be incorporated by reference.

We claim:

1. An isolated DNA molecule that encodes a naturally occurring glyphosate resistant plant-derived EPSPS enzyme wherein the glyphosate resistant plant-derived EPSPS enzyme has a $K_m$ for phosphoenolpyruvate (PEP) of less than 10 μM, and wherein the EPSPS enzyme comprises SEQ ID NO:7.

2. An isolated DNA molecule that encodes the naturally occurring glyphosate resistant EPSPS enzyme of SEQ ID NO: 7, wherein the DNA molecule has the nucleic acid sequence of SEQ ID NO: 6.

3. A recombinant DNA molecule comprising: a promoter that functions in plant cells, operably linked to a structural DNA sequence that encodes an EPSPS enzyme comprising the sequence of SEQ ID NO: 7, operably linked to a 3' non-translated region that functions in plant cells to cause the addition of polyadenyl nucleotides to the 3' end of the RNA sequence.

4. The recombinant DNA molecule of claim 3, wherein the promoter that functions in plant cells is heterologous to the structural DNA sequence.

5. The recombinant DNA molecule of claim 3, further comprising a DNA sequence operably linked to said structural DNA seauence encoding an amino-terminal chloroplast transit peptide.

6. A method of producing a glyphosate tolerant plant comprising the steps of:
   a) inserting into the genome of a plant cell a recombinant DNA molecule comprising: a promoter that functions in plant cells, operably linked to a structural DNA sequence that encodes an EPSPS enzyme having the sequence of SEQ ID NO: 7, operably linked to a 3' non-translated region that functions in plant cells to cause the addition of polyadenyl nucleotides to the 3' end of the RNA sequence; and
   b) regenerating from the transformed plant cell a genetically transformed plant which has increased tolerance to glyphosate herbicide as compared to an untransformed plant.

7. The method of claim 6, wherein the recombinant DNA molecule further comprises a DNA sequence operably linked to said structural DNA sequence encoding an amino-terminal chloroplast transit peptide.

8. A glyphosate tolerant plant cell comprising the recombinant DNA molecule of claim 3 or 5.

9. A glyphosate tolerant plant cell of claim 8 selected from the group consisting of corn, wheat, rice, millet, sugarcane, barley, oat, rye, turf grasses, asparagus, soybean, cotton, sugar beet, oilseed rape, canola, flax, sunflower, potato, tobacco, tomato, alfalfa, forest trees, fruit trees, ornamental annuals, and ornamental perennials.

10. The glyphosate tolerant plant comprising the plant cell of claim 8.

11. The glyphosate tolerant plant of claim 10 selected from the group consisting of corn, wheat, rice, millet, sugarcane, barley, oat, rye, turf grasses, asparagus, soybean, cotton, sugar beet, oilseed rape, canola, flax, sunflower, potato, tobacco, tomato, alfalfa, forest trees, fruit trees, ornamental annuals, and ornamental perennials.

12. Transgenic seed of the glyphosate tolerant transgenic plant of claim 11.

* * * * *